United States Patent
Nomura et al.

(10) Patent No.: US 12,343,456 B2
(45) Date of Patent: Jul. 1, 2025

(54) DISINFECTING AND VIRUS INACTIVATING DEVICE, AIR-CONDITIONING APPARATUS INCLUDING DISINFECTING AND VIRUS INACTIVATING DEVICE THEREON, AND DISINFECTION AND VIRUS INACTIVATION METHOD

(71) Applicant: Mitsubishi Electric Corporation, Tokyo (JP)

(72) Inventors: Akane Nomura, Tokyo (JP); Akinori Shimizu, Tokyo (JP); Yasuhiro Nakamura, Tokyo (JP); Seiro Yuge, Tokyo (JP); Koji Ota, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 18/692,839

(22) PCT Filed: Sep. 24, 2021

(86) PCT No.: PCT/JP2021/034958
§ 371 (c)(1),
(2) Date: Mar. 18, 2024

(87) PCT Pub. No.: WO2023/047508
PCT Pub. Date: Mar. 30, 2023

(65) Prior Publication Data
US 2024/0261454 A1    Aug. 8, 2024

(51) Int. Cl.
*A61L 9/22* (2006.01)
*A61L 2/20* (2006.01)
(Continued)

(52) U.S. Cl.
CPC ............... *A61L 9/122* (2013.01); *A61L 2/20* (2013.01); *A61L 2/24* (2013.01); *A61L 2202/14* (2013.01);
(Continued)

(58) Field of Classification Search
CPC .................................................. A61L 2202/25
See application file for complete search history.

(56) References Cited

U.S. PATENT DOCUMENTS

| 2009/0078121 A1* | 3/2009 | Hepburn | A61L 9/16 96/222 |
| 2015/0290348 A1 | 10/2015 | Taoka et al. | |

(Continued)

FOREIGN PATENT DOCUMENTS

| CN | 104971374 A | 10/2015 |
| JP | 2002-095728 A | 4/2002 |

(Continued)

OTHER PUBLICATIONS

JP_2016114283_A_Translation (Year: 2016).*

(Continued)

*Primary Examiner* — Sean E Conley
*Assistant Examiner* — Changru Chen
(74) *Attorney, Agent, or Firm* — XSENSUS LLP

(57) ABSTRACT

A disinfecting and virus inactivating device performs disinfection treatment or inactivation treatment in a target space that a moving body enters and exits. The disinfecting and virus inactivating device includes a locus detection module configured to detect a movement locus of locations where the moving body comes into contact with respective objects or respective portions of an object in the target space, a substance generating module configured to generate a particular substance for use in the disinfection treatment or the inactivation treatment, and a transmission module config- (Continued)

ured to generate an air flow and transmit the particular substance generated by the substance generating module to the movement locus.

13 Claims, 20 Drawing Sheets

(51) Int. Cl.
*A61L 2/24* (2006.01)
*A61L 9/12* (2006.01)

(52) U.S. Cl.
CPC ....... *A61L 2202/15* (2013.01); *A61L 2202/25* (2013.01); *A61L 2209/111* (2013.01); *A61L 2209/134* (2013.01); *A61L 2209/16* (2013.01)

(56) References Cited

U.S. PATENT DOCUMENTS

| | | | |
|---|---|---|---|
| 2019/0022263 A1 | 1/2019 | Quilici | |
| 2019/0117812 A1 | 4/2019 | Olsen et al. | |
| 2019/0192710 A1 | 6/2019 | Andersson et al. | |
| 2020/0073199 A1* | 3/2020 | Lin et al. | A61L 2/0047 |
| 2020/0101183 A1 | 4/2020 | Dijkstra et al. | |
| 2020/0297891 A1* | 9/2020 | Epperson | F24F 8/108 |

FOREIGN PATENT DOCUMENTS

| | | | | | |
|---|---|---|---|---|---|
| JP | 2004-150734 A | | 5/2004 | | |
| JP | 2016-114283 A | | 6/2016 | | |
| JP | 2017-072355 A | | 4/2017 | | |
| JP | 2019150564 A | | 9/2019 | | |
| JP | 2019-187653 A | | 10/2019 | | |
| JP | 2019-536492 A | | 12/2019 | | |
| JP | 2020067939 A | | 4/2020 | | |
| JP | 2020-070801 A | | 5/2020 | | |
| JP | WO2020039818 A1 | * | 8/2021 | ............... | A61L 9/01 |
| KR | 102136837 B1 | * | 7/2020 | ............... | A61L 2/24 |
| WO | WO-2018087171 A1 | * | 5/2018 | ............ | A47B 96/00 |
| WO | 2019142599 A1 | | 7/2019 | | |
| WO | 2020/039818 A1 | | 2/2020 | | |

OTHER PUBLICATIONS

JP_2017072355_A_Translation (Year: 2017).*
KR_102136837_B1_Translation (Year: 2020).*
JP_WO2020039818_A1_Translation (Year: 2021).*
International Search Report and Written Opinion mailed on Nov. 30, 2021, received for PCT Application PCT/JP2021/034958, filed on Sep. 24, 2021, 11 pages including English Translation.
Notice of Reason for Refusal mailed on May 10, 2022, received for JP Application 2022-514502, 6 pages including English Translation.
Decision to Grant mailed on Jun. 21, 2022, received for JP Application 2022-514502, 5 pages including English Translation.
Decision of Rejection dated Nov. 16, 2024 issued in corresponding CN patent application No. 202180102495.7 (and Machine Translation), 15pp.
Office Action dated Aug. 28, 2024 issued in corresponding CN patent application No. 202180102495.7 (and English translation), 13pp.
Office Action dated Sep. 4, 2024 issued in corresponding DE patent application No. 112021008001.6 (and English translation), 10pp.
Office Action issued on Jun. 22, 2024, in corresponding Chinese patent Application No. 202180102495.7, 15 pages.
Office Action dated May 6, 2025 issued in corresponding DE patent application No. 112021008001.6 (and Machine Translation), 8pp.

* cited by examiner

DISINFECTING AND VIRUS INACTIVATING DEVICE, AIR-CONDITIONING APPARATUS INCLUDING DISINFECTING AND VIRUS INACTIVATING DEVICE THEREON, AND DISINFECTION AND VIRUS INACTIVATION METHOD

CROSS-REFERENCE TO RELATED APPLICATION

This application is a national stage application, pursuant to 35 U.S.C. § 371, of International Patent Application No. PCT/JP2021/034958, filed Sep. 24, 2021, the entire contents of which are incorporated herein by reference.

TECHNICAL FIELD

The present disclosure relates to a disinfecting and virus inactivating device that performs disinfection or virus inactivation, an air-conditioning apparatus including the disinfecting and virus inactivating device, and a disinfection and virus inactivation method.

BACKGROUND ART

As substances that perform disinfection on and inactivate bacteria, molds, viruses, etc., for example, ions, ozone gas, hypochlorous acid water, and chlorine dioxide are present. Ions or ozone gas are generated by discharge. Hypochlorous acid water or chlorine dioxide is generated by electrolysis or chemical preparation, for example. By sending such a particular substance into a room using a fan, it is possible to disinfect the room for bacteria floating in air in the room, or to inactivate viruses.

Patent Literature 1 proposes a technique for disinfecting a predetermined region in a room after releasing ions generated by discharge into the predetermined region. In Patent Literature 1, the presence or absence of a person in the room is monitored by a human detecting sensor, a normal disinfection operation is performed while a person is present in the room, and a disinfection operation having a higher disinfection performance than the normal disinfection operation is performed after the person exits the room.

CITATION LIST

Patent Literature

Patent Literature 1: Japanese Unexamined Patent Application Publication No. 2016-114283

SUMMARY OF INVENTION

Technical Problem

In Patent Literature 1, when no person is present in the room, the disinfection operation having a higher disinfection performance than the normal disinfection operation is performed, thereby enhancing a disinfection effect in the room. However, actually, in the predetermined region in the room, bacteria, molds, viruses, etc., are not uniformly present, and bacteria, molds, viruses, etc., are unevenly spread because of the movement of a moving body, such as a person, who carries microorganisms including pathogenic microorganisms. Therefore, in the technique disclosed in Patent Literature 1, a particular substance released into the predetermined region in the room is partially wasted, and as a result, there is a possibility that disinfection or virus inactivation could not be efficiently performed in the room.

The present disclosure is applied in view of the above circumstances, and relates to a disinfecting and virus inactivating device that can efficiently perform disinfection or virus inactivation in a target space, an air-conditioning apparatus that includes the disinfecting and virus inactivating device, and a disinfection and virus inactivation method.

Solution to Problem

A disinfecting and virus inactivating device according to one embodiment of the present disclosure performs disinfection treatment or inactivation treatment in a target space that a moving body enters and exits. The disinfecting and virus inactivating device includes: a locus detection module configured to detect a movement locus of locations where the moving body comes into contact with respective objects or respective portions of an object in the target space; a substance generating module configured to generate a particular substance for use in the disinfection treatment or the inactivation treatment; and a transmission module configured to generate an air flow and transmit the particular substance generated by the substance generating module to the movement locus.

An air-conditioning apparatus according to another embodiment of the present disclosure includes: the above disinfecting and virus inactivating device; and a heat exchanger configured to cause heat exchange to be performed between air and refrigerant that flows in the heat exchanger. The air-conditioning apparatus transmits to the movement locus, an air flow that passes through the heat exchanger and is thus conditioned in temperature and that contains the particular substance.

A method for disinfection or virus inactivation, according to still another embodiment of the present disclosure, is a method of performing disinfection or virus inactivation in which disinfection treatment or inactivation treatment is performed in a target space that a moving body enters and exits. The method includes: detecting a movement locus of the moving body in the target space, as locus detection; and causing a transmission module to generate an air flow and transmit a particular substance generated by a substance generating module to the movement locus, as disinfection or inactivation.

Advantageous Effects of Invention

According to the embodiments of the present disclosure, it is possible to provide a disinfecting and virus inactivating device that can efficiently perform bacteria disinfection or virus inactivation in a target space, to provide an air-conditioning apparatus in which the disinfecting and virus inactivating device is mounted, and to provide a method of performing disinfection or virus inactivation.

BRIEF DESCRIPTION OF DRAWINGS

FIG. 19 is a schematic view of a modification of the air-conditioning apparatus 60 according to Embodiment 3 as viewed side-on.

DESCRIPTION OF EMBODIMENTS

Figure 1:
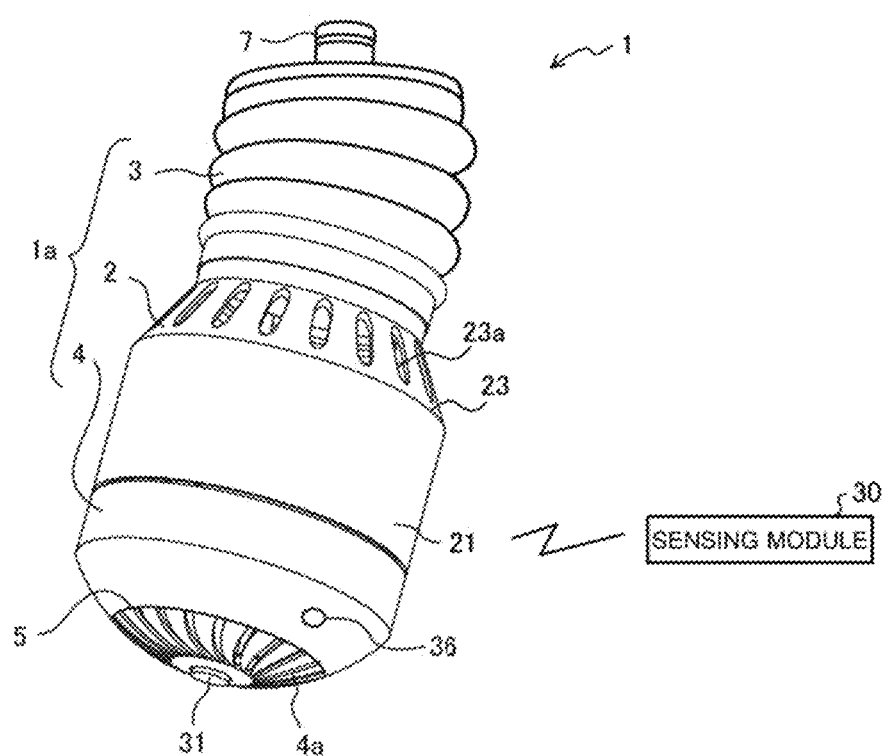
FIG. 1 is an external appearance view of a disinfecting and virus inactivating device according to Embodiment 1.

The embodiments according to the present disclosure will be described with reference to the accompanying drawings. In each of the figures in the drawings, components that are the same as or equivalent to those in a previous figure or previous figures are denoted by the same reference signs, and their descriptions will thus be omitted or simplified as appropriate. For example, the shapes, the sizes and the arrangement of components described in each of the figures may be appropriately modified within the scope of the present disclosure.

Embodiment 1

Regarding Embodiment 1, a disinfecting and virus inactivating device 1 for use in, for example, a space of an office, will be described by way of example.

Before the disinfecting and virus inactivating device 1 will be described, transmission routes of germs or viruses will be described. In the present disclosure, targets for disinfection or inactivation are microorganisms including pathogenic microorganisms, such as bacteria or viruses. As the transmission, for example, droplet transmission, contact transmission, and aerial transmission are present. The droplet transmission is a transmission that occurs when bacteria or viruses contained in "droplets", such as saliva, which fly off by a cough or a sneeze come into contact with a membrane of a mouth or a nose. The contact transmission is a transmission that occurs when an infected person covers a sneeze or a cough with his or her hand and then touches an object located close to the person with the hand, and another person then touches the object and is infected through a membrane of his or her mouth or nose.

The aerial transmission is a transmission that occurs through fine particles containing bacteria or viruses that are far smaller than droplets present in the air, specifically, through fine particles generated by a cough or a sneeze, or through particles generated through evaporation of moisture of droplets. That is, the aerial transmission is a transmission caused by bacteria or viruses contained in fine particles smaller than droplets. As the fine particles containing bacteria or viruses that are far smaller than the droplets, particles originally generated as fine particles at the time of coughing or sneezing, and particles generated through evaporation of moisture from droplets scattered in the air, are present.

The droplets are heavy, and thus fall onto a floor surface immediately after coughing or sneezing. It is possible to prevent scattering of droplets by using masks. The bacteria or viruses present in the air are easily devitalized when they fall onto the floor surface, adhere to a wall, or dry (Naohide Shinohara, Reference researches on indoor environment valuable for infection control of coronavirus [first edition], Society of Indoor Environment, Japan [2020]). However, it is confirmed that bacteria or viruses adhering to furniture in a room due to contact of a person or falling of droplets from a person maintains activity for a time period that is at least two times longer than bacteria or viruses present in the air. In view of the above, in order to reduce the risk of transmission from bacteria or viruses, it is considered important to apply a technique for preventing the contact transmission, specifically, a technique for performing disinfection on bacteria adhering to furniture in a room or a technique for inactivating viruses. At the moment, such techniques are required. It should be noted that the furniture is equipment and fixtures that are present in a predetermined space. In the indoor space of a common household, the furniture corresponds to tables and counters. In the indoor space of an office, the furniture corresponds to equipment for use in daily life that is present in the space, such as work tables, desks, and shelves.

Figure 2:
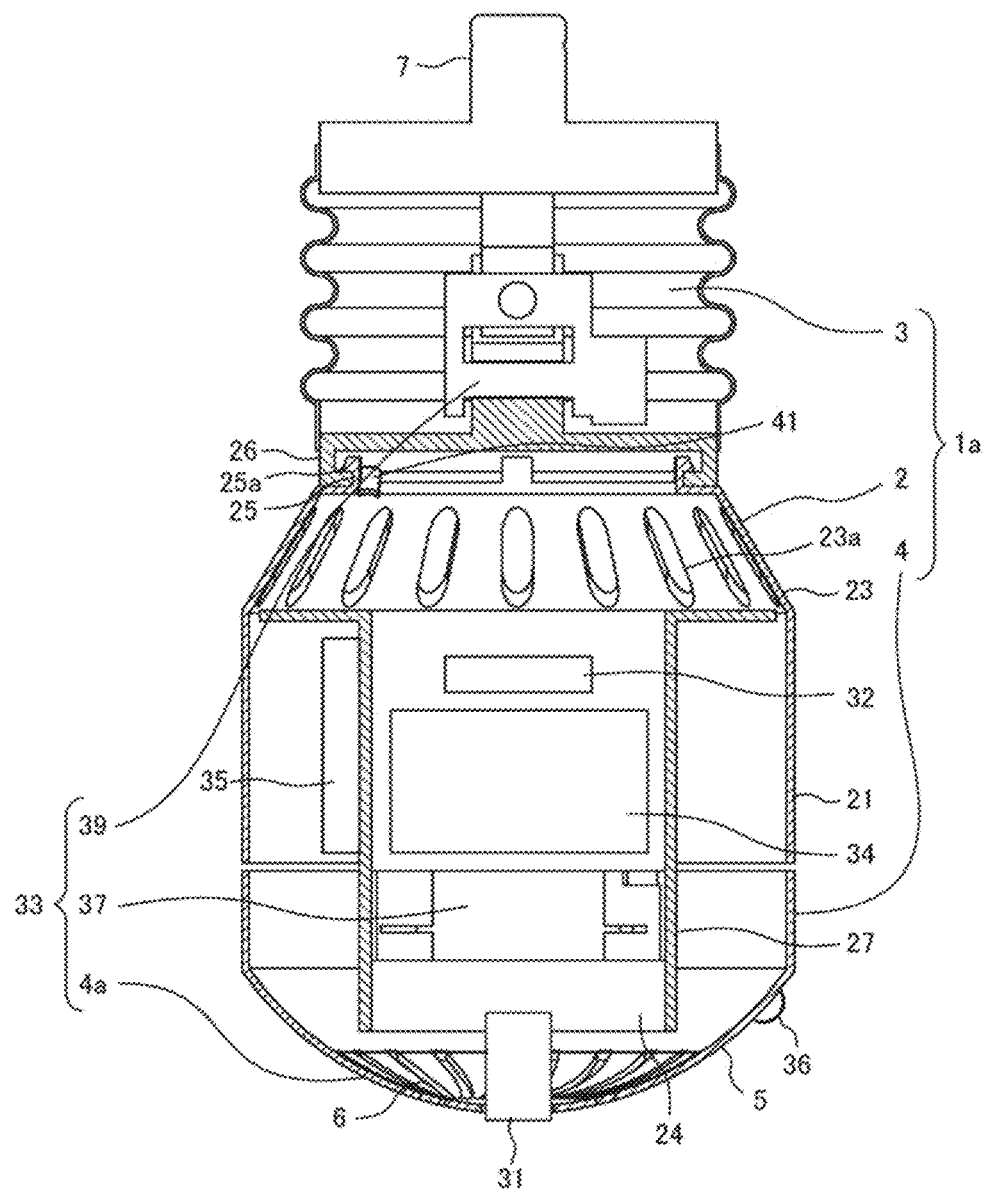
FIG. 2 schematically illustrates an example of a section of the disinfecting and virus inactivating device according to Embodiment 1.
Figure 3:
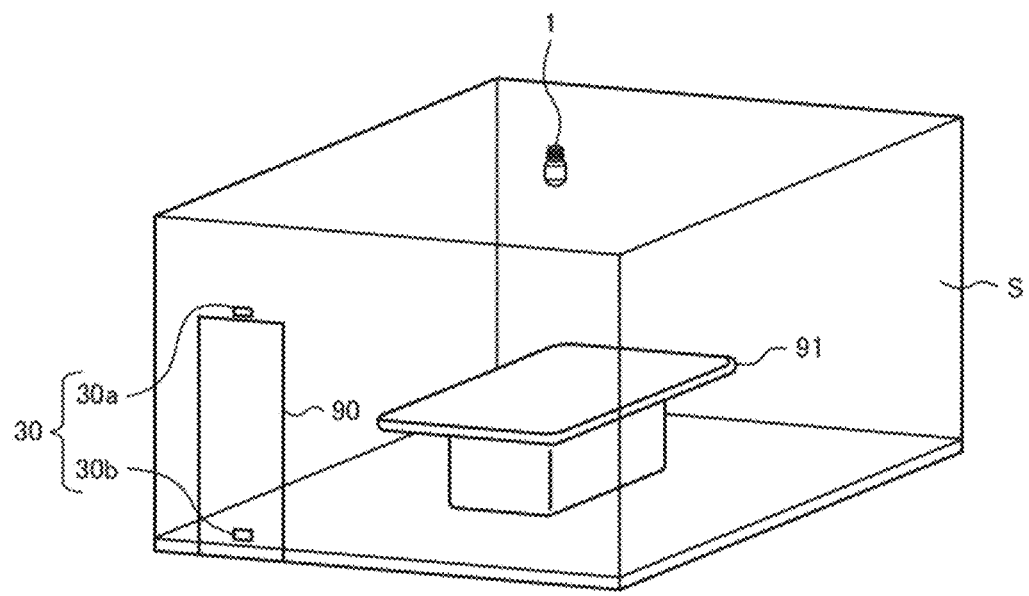
FIG. 3 illustrates a usage form of the disinfecting and virus inactivating device according to Embodiment 1.

FIG. 1 is an external appearance view of the disinfecting and virus inactivating device 1 according to Embodiment 1. FIG. 2 schematically illustrates an example of a section of the disinfecting and virus inactivating device 1 according to Embodiment 1. FIG. 3 illustrates a usage form of the disinfecting and virus inactivating device 1 according to Embodiment 1. In the following description, directions, such as "up" and "down", are defined with reference to an installation-state of the disinfecting and virus inactivating device 1 as illustrated in FIGS. 1 to 3.

The disinfecting and virus inactivating device 1 is installed at a high position, such as at a ceiling, in a target space S to be subjected to bacteria disinfection or virus inactivation and transmits a particular substance for disinfection treatment or inactivation treatment into the target space S. The target space S is a closed space that a person enters and exits. For example, the target space S is partitioned off by partitions and has a door 90 that is used when the person enters and exits the space. The target space S is, for example, an office. In the target space S, furniture 91, such as a work table and a chair, is set.

A housing 1a of the disinfecting and virus inactivating device 1 includes a first casing 2, a second casing 3, and a grille body 4. The second casing 3 is detachably attached to an upper portion of the first casing 2, and the grille body 4 is detachably attached to a lower portion of the first casing 2. The upper end portion of the housing 1a has a base 7 that is to be connected to a fixing jig portion set at a high place, for example, a ceiling. The disinfecting and virus inactivating device 1 is configured such that when the base 7 is attached to the fixing jig portion, commercial power is supplied to a power supply device (which will be described later) via the base 7. A display module 36 that displays an operation state of the disinfecting and virus inactivating device 1 is attached to an outer wall of the housing 1a, that is, it is attached to an outer wall of the grille body 4 as illustrated in FIG. 1. The disinfecting and virus inactivating device 1 further includes a sensing module 30 that is connected to a communication module 42 (which will be described later) in the first casing 2 such that the sensing module 30 can communicate with the communication module 42 (see FIG. 5). The sensing module 30 is provided separate from the housing 1a.

The first casing 2 includes a cylindrical portion 21 that has a cylindrical shape, and an upper surface portion 23 that has an annular shape and covers an opening formed in an upper end of the cylindrical portion 21. The upper surface portion 23 has a plurality of air inlets 23a through which air is sucked from the outside, and which are arranged at intervals in a circumferential direction. A filter (not illustrated) is detachably provided on an inner surface side of each of the air inlets 23a. An air-passage forming portion 27 having a cylindrical shape is fixed in the first casing 2, and a ventilation passage 24 is formed in the air-passage forming portion 27. The air-passage forming portion 27 communicates with the air inlets 23a. Also, an upstream side of the ventilation passage 24 communicates with the air inlets 23a. A downstream side of the ventilation passage 24 is located in the grille body 4. An air flow that flows out from an outlet of the ventilation passage 24 flows into the grille body 4, and is blown out to the outside through a grille 4a (which will be described later) of the grille body 4. The outer shape of the housing 1a is not limited to the above shape, and may be any shape. For example, the cylindrical portion 21 of the first casing 2 is formed in the shape of a cylinder having a rectangular sectional shape.

A connector 25 is provided at the upper surface portion 23 of the first casing 2 in order to connect the first casing 2 to the second casing 3. The connector 25 forms part of the first casing 2. The first casing 2 is detachably attached to the second casing 3 when a hook portion 25a provided at the connector 25 is engaged with an engagement portion 26 provided at a lower end portion of the second casing 3. A mode changing switch 41 (which will be described later) is provided at the connector 25.

The second casing 3 is provided to change the flow direction of an air flow that is blown out from the grille body 4, and is formed of material having a bellows shape and flexibility. FIG. 1 illustrates a state in which the flow direction of the air flow blown out from the grille body 4 is changed from a vertically downward direction to an oblique direction.

The grille body 4 is provided in such a manner as to cover an opening of the ventilation passage 24 of the first casing 2 that is located on the outlet side, and is located on a center axis of the ventilation passage 24. Although not illustrated in detail, the grille body 4 is supported by an inner wall of the first casing 2. The grille body 4 includes the grille 4a at the lower portion thereof. The grille 4a forms part of a transmission module 33 (which will be described later) and will be re-described later.

In the housing 1a, a locus detection module 31, a substance generating module 32, the transmission module 33, a substance measuring module 34, and a main board 35 are provided.

Each of components that form the disinfecting and virus inactivating device 1 will be described.

Description of Sensing Module 30

The sensing module 30 detects that a moving body enters the target space S and also that the moving body exits the target space S (hereinafter referred to as entry/exit). The sensing module 30 may be an infrared sensor, for example. The sensing module 30 is capable of communicating with the communication module 42 (which will be described later) and thus capable of sending the result of detection of the moving body to the communication module 42. The communication module 42 is provided in the housing 1a. As this communication, wireless communication, such as wireless LAN, Bluetooth (registered trademark), or ZigBee (registered trademark), is used. It should be noted that a sensing module already provided in the target space S may be used as the sensing module 30.

Explanation of Locus Detection Module 31

The locus detection module 31 detects a movement locus of locations where the moving body comes into contact with respective objects or respective portions of an object. The locus detection module 31 is provided at a central portion of a lower end of the grille body 4. The moving body, which is a locus detection target, is any of various moving bodies, for example, a person, living bodies including pets, such as a dog and a cat, and mobile equipment, such as a mobile vacuum cleaner. In the following description, it is assumed that the moving body is a person unless otherwise specified. A configuration and operation of the locus detection module 31 will be described in detail.

Explanation of Substance Generating Module 32

The substance generating module 32 generates a particular substance, such as ions, ozone gas, chlorine dioxide, or hypochlorous acid water, which can destroy or inactivate microorganisms including pathogenic microorganisms that are carried by a person. The substance generating module 32 is attached to an inner wall of the air-passage forming portion 27. In Embodiment 1, the substance generating module 32 includes a discharge mechanism that generates ions. The discharge mechanism is provided in such a manner as to face the ventilation passage 24 in the first casing 2. The discharge mechanism is configured such that a discharge module and an electrode cover that covers the discharge module are provided in a casing, thus forming a unit. Furthermore, a control circuit board on which, for example, a high voltage generation circuit is mounted is incorporated in the discharge mechanism. The control circuit board is provided with a connector that supplies power from the outside.

The discharge module includes discharge electrodes and ground electrodes. The discharge electrodes are wire electrodes, and the ground electrodes are plate electrodes. In the discharge module, the wire electrodes and the plate electrodes are alternately arranged. A high voltage is supplied from the high voltage generation circuit to the discharge module. The high voltage generation circuit includes a power reception module that receives power from the commercial power supply. The high voltage generation circuit converts the power received by the power reception module through the connector and an electric wire, into a high voltage, and supplies the high voltage to the discharge module. The discharge module applies the high voltage supplied from the high voltage generation circuit between the discharge electrodes and the ground electrodes, thereby causing discharge and thus causing ions to be generated in the air. In the present embodiment, in the discharge module, each of the discharge electrodes is a wire electrode and each of the ground electrodes is a plate electrode. However, such a configuration is merely an example, and each of the discharge electrodes and each of the ground electrodes may be any of a wire electrode, a needle electrode, a plate electrode, and a brush electrode.

Explanation of Transmission Module 33

The transmission module 33 generates an air flow having high straightness and high directivity. The transmission module 33 includes a blower 37, the grille 4a, and a driving device 39. The blower 37 generates an air flow, the grille 4a gives straightness and directivity to the air flow, and the driving device 39 drives the first casing 2 such that the air flow given the straightness by the grille 4a is transmitted toward the movement locus (which will be described later).

Blower 37

The blower 37 includes a blowing fan and a motor that drives the fan. The fan is provided close to the outlet of the ventilation passage 24, and is supported on the inner wall of the first casing 2 and located on the center axis of the ventilation passage 24. In order to generate a large amount of air flow, an axial-flow-type propeller fan is adopted as the fan. Furthermore, an AC capacitor motor is adopted as the fan motor. When the fan of the blower 37 is driven, air around the first casing 2 is sucked into the first casing 2 in a radial direction thereof through the air inlets 23a, and flows into the inlet of the ventilation passage 24. The direction of the air flow that has flowed into the inlet of the ventilation passage 24 changes from the radial direction to the axial direction. The air that flows in the ventilation passage 24 in the axial direction is blown out from the outlet of the ventilation passage 24 to the outside of the housing 1a through the grille 4a.

The blower 37 is provided in the ventilation passage 24 and downstream of the substance generating module 32. With such a configuration, the particular substance generated by the substance generating module 32 is mixed with air within the fan of the blower 37, and is then blown out to the outside of the housing 1a, with the ion concentration in the air uniformized.

Grille 4a

Figure 4:
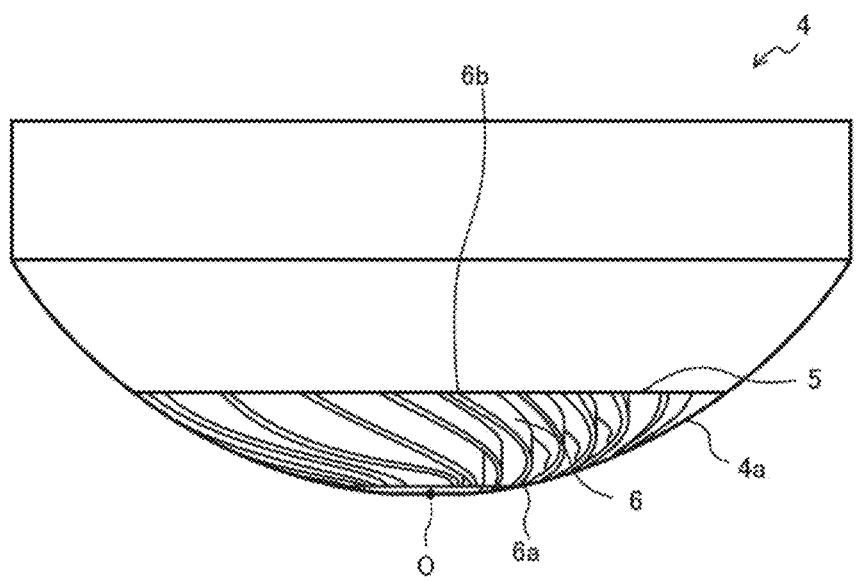
FIG. 4 is a perspective view illustrating a grille body of the disinfecting and virus inactivating device according to Embodiment 1.

FIG. 4 is a perspective view illustrating the grille body 4 of the disinfecting and virus inactivating device 1 according to Embodiment 1. The grille body 4 has a blowing port 5, and the grille 4a is provided in the blowing port 5. The grille 4a includes a plurality of fins 6 having a spiral shape. The grille 4a has a structure in which inner end portions 6a of the fins 6 further protrude in the blowing direction than outer end portions 6b of the fins 6. The inner end portions 6a is located close to a central portion O of the spiral of the fins 6, and the outer end portions 6b is formed continuous with the blowing port 5. In other words, the grille 4a is configured such that the inner end portions 6a of the fins 6 further protrude in the blowing direction than the outer end portions 6b of the fins 6. Each of the inner end portions 6a is located on an inner end side close to the central portion O of the spiral, and part of the inner end portion 6a is close to an inner end. Each of the outer end portions 6b is located on an outer end side that is continuous with the blowing port 5.

With such a configuration, the grille 4a can collect and converge at the center, the air flow that has flowed out from the outlet of the ventilation passage 24 and flowed into the grille body 4, thus increasing the velocity of the air flow in the blowing direction at the center. Furthermore, the grille 4a can increase the reach of a spiral air flow blown out from the blowing port 5. For these reasons, the grille 4a can give straightness and directivity to the air flow generated by the blower 37.

Driving Device 39

FIGS. 1 and 2 will be re-referred to. The driving device 39 changes the orientation of the grille 4a and controls the orientation of the grille 4a, by driving the first casing 2 such that the air flow blown out from the grille 4a flows toward the movement locus detected by the locus detection module 31. When the driving device 39 drives the first casing 2, the second casing 3 having a bellows shape is deformed, thereby changing the blowing direction. The driving device 39 includes a motor (not illustrated) that can drive two shafts that are orthogonal to each other. The motor is a general servomotor or a stepping motor. Each of these motors can control the angle of a shaft that supports the first casing 2, and can stop the shaft that supports the first casing 2, at a particular position. Thus, the driving device 39 can accurately stop the grille 4a, which is provided in the blowing port 5, such that the grille 4a is made to face the movement locus.

Because having the above configuration, the transmission module 33 can change the air flow generated by the blower 37 into an air flow having straightness and directivity that are improved by the grille 4a, and transmit the air flow toward the movement locus.

Explanation of Substance Measuring Module 34

The substance measuring module 34 includes an ion sensor that measures a discharge product in the air. The ion sensor is provided in the ventilation passage 24 located downstream of the substance generating module 32 in the flow direction of the air flow. A coaxial double cylindrical sensor that measures positive ions or negative ions in the air is adopted as the ion sensor. With such a configuration, the ion sensor can measure positive ions and negative ions at the same time, and can measure a concentration within a wide range of 100,000 to 3,000,000 (ions/cm$^3$) with high accuracy. The result of measurement by the substance measuring module 34 is outputted to a controller 40 (which will be described later). In the case where the particular substance generated by the substance generating module 32 is ozone, the substance measuring module 34 is an ozone gas sensor that measures ozone in the air.

Explanation of Display Module 36

The display module 36 is attached to the outer wall surface of the grille body 4 as an electronic component that transmits information. The display module 36 is, for example, a light emitting diode (LED) that makes notifications for various kinds of information. The display module 36 displays the operation state of the disinfecting and virus inactivating device 1 by changing a lighting state of the light emitting diode. The display module 36 can change the lighting state by appropriately combining an emission color of the light emitting diode and a lighting mode, such as blinking or continuous lighting. By changing the lighting state of the light emitting diode, the display module 36 can make a display indicating that the locus of a person is being detected, or can make a notification for abnormality.

Explanation of Main Board 35

The main board 35 includes the controller 40 (see FIG. 5 which will be described later), a power supply device, and other components thereon. The controller 40 controls the entire disinfecting and virus inactivating device 1. The power supply device supplies power to each of the components. The main board 35 is fixed to a side wall of the air-passage forming portion 27 of the first casing 2. The controller 40 is, for example, a microprocessor unit, and includes a CPU, a RAM, a ROM, and other components. A control program and other programs are stored in the ROM.

The controller 40 controls the locus detection module 31, the substance generating module 32, the blower 37, and the driving device 39 based on the result of detection by the sensing module 30 with respect to entry/exit of a person. The controller 40 performs a locus detection operation and a disinfection/inactivation operation. These operations will be described later. The controller 40 also controls the display module 36 based on the result of measurement by the substance measuring module 34. To be more specific, when the controller 40 detects, from the result of the result of the measurement by the substance measuring module 34, that the concentration of the particular substance is less than or equal to a set concentration set in advance, the controller 40 stops the operation of the substance generating module 32, and causes the display module 36 to be lit. To be more specific, the controller 40 controls the display module 36 to cause the display module 36 to be in a lighting state indicating occurrence of an abnormality in the substance generating module 32. In such a manner, the disinfecting and virus inactivating device 1 can make a notification indicating occurrence of abnormality.

Figure 5:
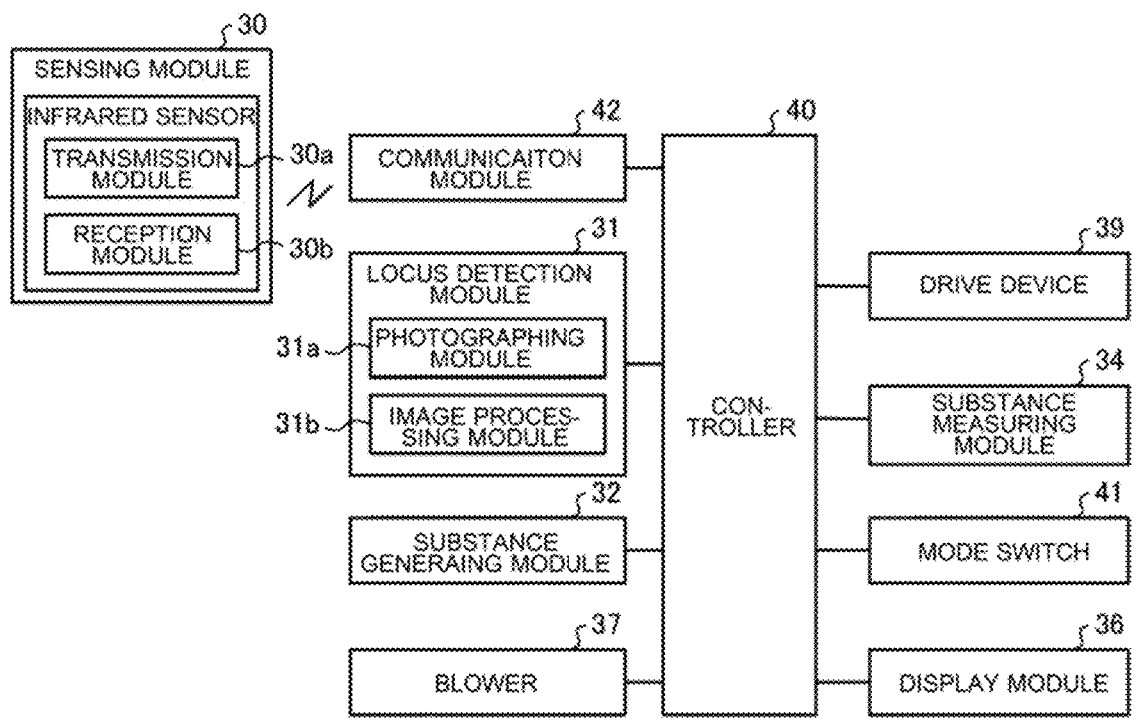
FIG. 5 is a block diagram of the disinfecting and virus inactivating device according to Embodiment 1.

FIG. 5 is a block diagram of the disinfecting and virus inactivating device 1 according to Embodiment 1.

The locus detection module 31, the substance generating module 32, the blower 37, the driving device 39, the substance measuring module 34, the mode changing switch 41, and the display module 36 are electrically connected to the controller 40 by leads. The communication module 42 is also electrically connected to the controller 40 by a lead. The communication module 42 has a function of performing wireless communication, such as wireless LAN, Bluetooth (registered trademark), or ZigBee (registered trademark), and performs wireless communication with the sensing module 30.

The disinfecting and virus inactivating device 1 performs wireless communication with the sensing module 30 via the communication module 42 to detect entry/exit of a person. To be more specific, the disinfecting and virus inactivating device 1 obtains, through the communication module 42, a sensing signal indicating entry/exit of a person and sent from the sensing module 30, and detects the entry/exit of a person based on the sensing signal. The disinfecting and virus inactivating device 1 detects entry of a first person and exit of all persons, based on a sensing signal sent from the sensing module 30. The disinfecting and virus inactivating device 1 may use, as the sensing module 30, a sensor already provided in the target space S.

The infrared sensor included in the sensing module 30 includes a transmission module 30a and a reception module 30b. The transmission module 30a sends infrared rays, and the reception module 30b receives the infrared rays. The transmission module 30a and the reception module 30b are installed close to the door 90 of the target space S. To be more specific, the transmission module 30a and the reception module 30b are provided above and below an entrance, respectively, and infrared rays are transmitted from the transmission module 30a and received by the reception module 30b.

When no person passes through an area located between the transmission module 30a and the reception module 30b, the amount of infrared rays that are received by the reception module 30b does not change, that is, the reception module 30b receives a substantially constant amount of infrared rays. In contrast, when a person passes through the area, the amount of infrared rays that are received by the reception module 30b decreases. When the amount of infrared rays received by the reception module 30b falls below a specified value, the infrared sensor detects movement of a person. A method of detecting entry/exit of a person using an infrared sensor is simpler and can achieve a device configuration at a lower cost than a method of detecting entry/exit of a person using image data.

As described above, the sensing module 30 may be installed close to the door 90, and for example, in the case where the target space S is a toilet, the sensing module 30 may be installed close to a toilet bowl in the toilet.

The locus detection module 31 performs detection processing to detect a movement locus of points of contact of the moving body, at which the moving body comes into contact with respective objects or respective portions of an object; that is, a movement locus of locations where the moving body comes into contact with respective objects or respective portions of an object. The movement locus is a locus of locations where a person comes into contact with respective objects or respective portions of an object, such as locations where the person's hand touches the respective objects or respective portions of an object and locations where the person walks. However, in the following description, of the portions where the person touches the respective objects or respective portions of an object, positions where the person touches respective objects or respective portions of an object whose infection risks are high are considered, and a movement locus of these positions is detected. To be more specific, it is assumed that the movement locus is a locus of locations where the person touches respective portions of the furniture 91.

The locus detection module 31 includes a photographing module 31a and an image processing module 31b. The photographing module 31a photographs the target space S, and the image processing module 31b performs locus detection based on photographic data from the photographing module 31a.

Photographing Module 31a

The photographing module 31a photographs the inside of the target space S. The photographing module 31a includes an imaging element, a lens module, a lens holder, and a cover plate. The imaging element includes a solid-state imaging element, such as a complementary metal oxide semiconductor (CMOS) image sensor or a charge coupled device (CCD) image sensor, which can obtain image data. The lens module is provided in a front portion of the imaging element. The lens module includes a lens and an adjusting module. The lens focuses light, and the adjusting module relatively displaces the imaging element and the lens from each other. The adjusting module includes a permanent magnet and an electromagnetic coil. The permanent magnet holds the lens, and the electromagnetic coil causes the permanent magnet to move.

The lens module causes the lens to move by adjusting a current that flows in the coil in order to adjust the focal point of the imaging element. The lens holder holds the lens module. The lens holder has an annular outer shape. The cover plate is provided in such a manner as to close an opening of the annular lens holder. The cover plate is provided in front of the lens module. The cover plate has light transmitting properties. The cover plate is colored to prevent the inside of the photographing module 31a from being easily visually viewable from the outside.

Image Processing Module 31b

The image processing module 31b includes an arithmetic control module, a first storage module, and a second storage module. The arithmetic control module performs arithmetic processing on image data obtained by imaging by the photographing module 31a. The arithmetic control module includes a field programmable gate array (FPGA) and a digital signal processor (DSP). The arithmetic control module may use, instead of the DSP, a semiconductor element, such as an advanced image processor, which can perform digital image processing at a high speed.

The first storage module stores image data obtained in advance by imaging by the photographing module 31a that is performed when no person is present in the target space S. The image data obtained in advance by imaging that is performed when no person is present is used as background data in moving-body detection processing for discrimination between a person and objects other than the person. In order that the image data be transferred to the arithmetic control module at a high speed, a nonvolatile memory such as synchronous DRAM (SDRAM) is used as the first storage module.

The second storage module stores, as image data, tracking data on a person present in the target space S. In order to store a large amount of image data, a large-capacity storage device is used as the second storage module. The large-capacity storage device is a volatile memory having a relatively large storage capacity, such as a dynamic random access memory (DRAM).

The image processing module 31b causes the first storage module to store background data. The image processing module 31b appropriately causes the arithmetic control module to read the background data stored in the first storage module. The image processing module 31b causes the arithmetic control module to read current image data obtained by imaging that is periodically performed by the photographing module 31a.

The arithmetic control module performs image difference processing, using the read current image data and background data. The image difference processing is processing in which the current image data is compared with the background data, a difference image is produced by obtaining a difference with respect to each of pixels, and the obtained difference image is subjected to binarization processing using a threshold set in advance, thereby producing a binary image. In the case of producing the difference image, the comparison is not limited to the above comparison using the background data. That is, in order to produce the difference image, two image data that is read at different timings by an imaging element may be compared with each other to obtain a difference between the two image data.

Regarding pixels in which no change is made between the current image data and the background data, a luminance value for the difference between those pixels is lower than a threshold set in advance. In contrast, regarding pixels in which a change is made between the current image data and the background data, that is, pixels of image part obtained by photographing a person, a luminance value for the difference between those pixels is higher than the threshold set in advance. The arithmetic control module extracts the image part where the person is photographed, by performing, by using the threshold, binarization processing on a difference image between the current image data and the background data.

The arithmetic control module causes the second storage module to record, as a location where the person is present, a binary image obtained by performing image processing to extract the location where the person is present. Each time image data is outputted from the imaging module, the arithmetic control module performs image difference processing to produce a binary image, and causes the second storage module to store the produced binary image. The arithmetic control module can detect the movement locus of the person who is present in the target space S from binary images that are stored in the second storage module in time series. That is, by comparing a current binary image with a binary image produced a given period of time ago, the arithmetic control module can track the movement of the person. While the locus detection module 31 is performing tracking the person that continues until the person exits the target space S, the arithmetic control module continuously causes the second storage module to store locus detection data associated with binary images.

The arithmetic control module recognizes in advance a location where the furniture 91 is provided, based on background data, and can detect a location where the person comes into contact with the furniture, from a positional relationship between the location where the furniture is provided and the location where the person is present. To be more specific, the arithmetic control module obtains in advance a difference image between image data on a state in which the furniture 91 is not installed and image data on a state in which the furniture 91 is installed, that is, obtains a difference image by extracting the furniture 91. The arithmetic control module detects, as the location that the person comes into contact with the furniture 91, a portion at which the difference image obtained by extracting the furniture 91 overlaps with a binary image obtained by extracting the location where the person is present.

By performing the above operations, the locus detection module 31 can detect the movement locus of locations where the person comes into contact with respective objects or respective portions of an object in the target space S. This movement locus includes a movement locus of the positions of parts of the ground with which the person comes into contact while walking or a movement locus of contact positions at which the person comes into contact with the furniture 91 by hand.

Mechanism for Improving Disinfection/Inactivation Effect

Next, it will be described how the disinfecting and virus inactivating device 1 efficiently performs bacteria disinfection or virus inactivation on the furniture 91 in the target space S.

In general, the particular substance exhibits a bacteria disinfection or virus inactivation effect (hereinafter referred to as "disinfection/inactivation effect") when the concentration of the particular substance reaches a certain threshold or more. When the concentration of the particular substance is further increased, the bactericidal effect is rapidly improved.

Figure 6:
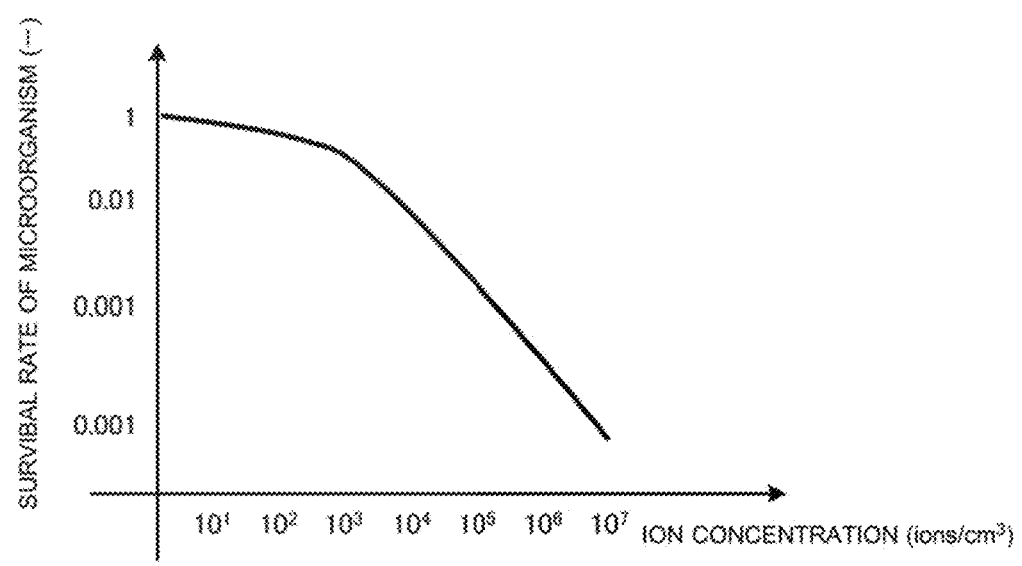
FIG. 6 is a graph illustrating a relationship between ion concentration and a disinfection/inactivation effect.

FIG. 6 is a graph illustrating a relationship between an ion concentration and disinfection/inactivation effect. In FIG. 6, the horizontal axis represents the ion concentration (ions/$cm^3$) and the vertical axis represents the survival rate (−) of a microorganism.

When the ion concentration increases to reach $10^3$ (ions/$cm^3$) or more, the disinfection/inactivation effect is exhibited, and when the ion concentration further increases, the disinfection/inactivation effect is further enhanced. Therefore, the substance generating module 32 is configured to generate ions having an ion concentration of 103 (ions/cm$^3$) or more.

Operations

The disinfecting or virus inactivating device 1 performs the locus detection operation and the disinfection/inactivation operation. First, the locus detection operation will be described, and next, the disinfection/inactivation operation will be described.

Locus Detection Operation

The locus detection operation is performed when a person is present in the target space S, and the locus detection operation is an operation to detect the movement locus of locations where the person comes into contact with respective objects or respective portions of an object.

Figure 7:
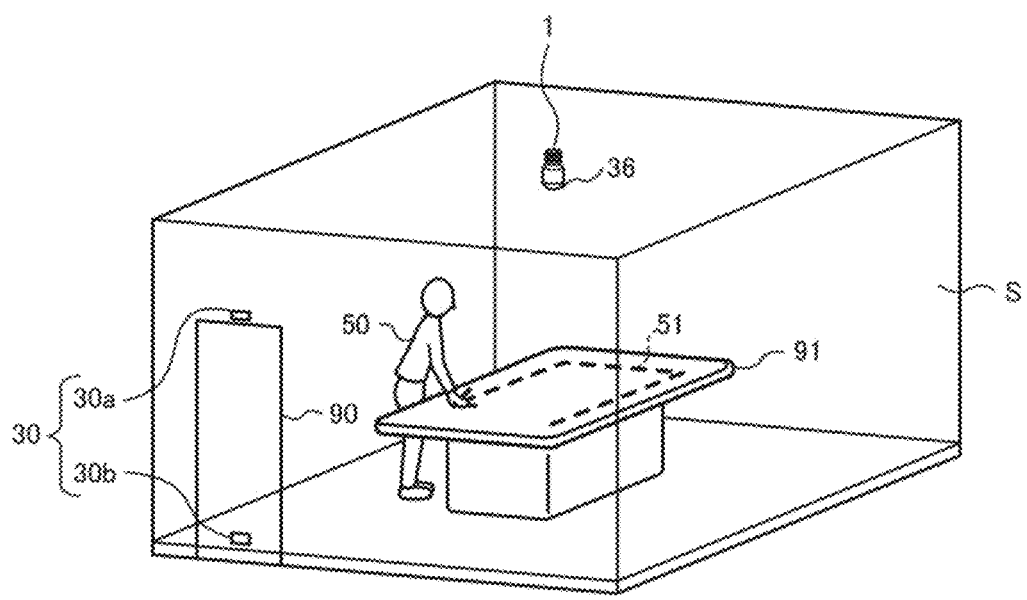
FIG. 7 is an explanatory view for a locus detection operation of the disinfecting and virus inactivating device according to Embodiment 1.

FIG. 7 is an explanatory view for the locus detection operation of the disinfecting or virus inactivating device 1 according to Embodiment 1.

In the locus detection operation, the sensing module 30 detects entry/exit of a person 50 into/from the target space S. In the locus detection operation, when the sensing module 30 detects entry of the person 50 into the target space S, the disinfecting and virus inactivating device 1 starts detection of the movement locus of locations where the person 50 comes into contact with respective objects or respective portions of an object. The disinfecting and virus inactivating device 1 continues detection of the movement locus of locations where the person 50 comes into contact with respective objects or respective portions of an object, until the sensing module 30 detects exit of the person 50 from the target space S. In FIG. 7, a dashed arrow indicates a movement locus 51 of the person 50, that is, contact positions where the person 50 comes into contact with respective portions of the furniture 91.

During the locus detection operation, the disinfecting and virus inactivating device 1 causes the display module 36 to be lit in a lighting manner indicating that the disinfecting and virus inactivating device 1 is performing the locus detection operation. With such an operation, the disinfecting and virus inactivating device 1 can make a notification indicating the contents of the operation.

Disinfection/Inactivation Operation

In the disinfection/inactivation operation, bacteria disinfection or virus inactivation is performed on the target space S in order to reduce the risk of contact transmission.

Figure 8:
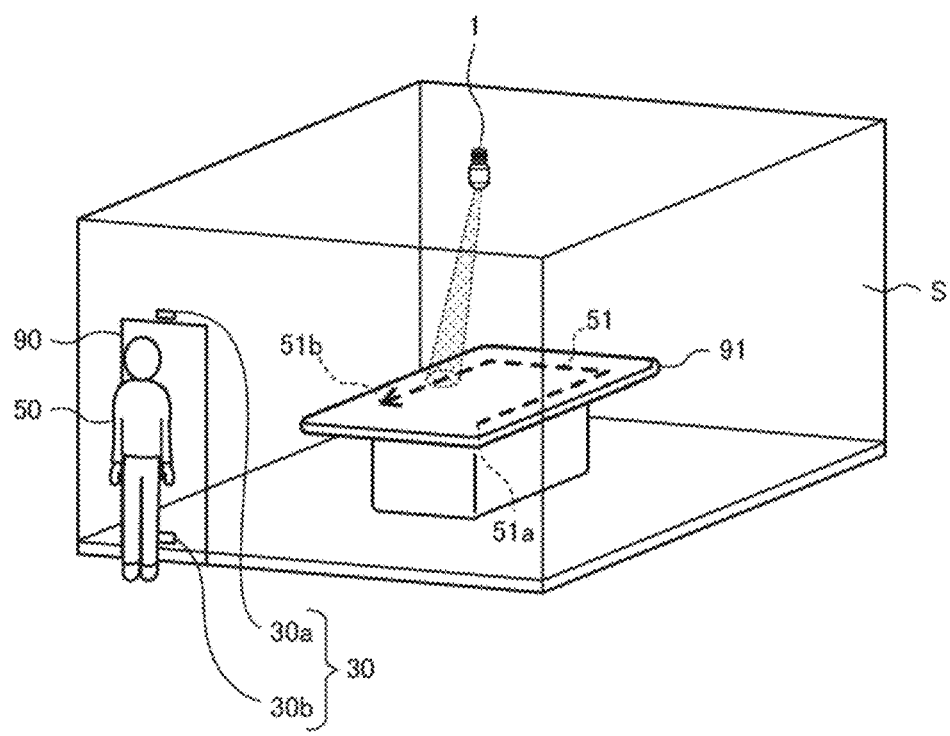
FIG. 8 is an explanatory view for a disinfection/inactivation operation of the disinfecting and virus inactivating device according to Embodiment 1.

FIG. 8 is an explanatory view for the disinfection/inactivation operation of the disinfecting and virus inactivating device 1 according to Embodiment 1. The disinfection/inactivation operation is performed when the person 50 exits the target space S. In the disinfection/inactivation operation, a particular substance generated by the substance generating module 32 is transmitted in such a manner as to describe the movement locus 51 as indicated in FIG. 8. The disinfection/inactivation operation is performed until the sensing module 30 detects entry of the person 50.

When the sensing module 30 detects exit of the person 50, the disinfecting and virus inactivating device 1 starts the disinfection/inactivation operation by driving the substance generating module 32 and the transmission module 33. To be more specific, the controller 40 drives the substance generating module 32 to generate the particular substance, and starts the operation of the blower 37, thereby starting the disinfection/inactivation operation. Ions that are the particular substance generated by the substance generating module 32 are conveyed together with an air flow toward the outlet of the ventilation passage 24 by the operation of the blower 37. At the same time, the controller 40 controls the driving device 39 to cause the grille 4a of the grille body 4 to face in a direction along the movement locus 51 detected by the locus detection module 31.

With such operations, the particular substance generated by the substance generating module 32 is transmitted toward the movement locus 51 of the person 50 in the target space S by an air flow having straightness and directivity increased by the grille 4a. The disinfecting and virus inactivating device 1 transmits the particular substance such that the particular substance describes the movement locus 51 from a start point 51a toward an end point 51b, by controlling the orientation of the grille 4a of the grille body 4.

The movement locus 51 is a movement locus of the person 50 who carries bacteria or viruses, and is a locus of locations where a large number of bacteria or viruses adhere to respective objects or respective portions of an object in the target space S. By virtue of the present structure, it is possible to transmit the particular substance with an air flow having high straightness and high directivity toward the movement locus 51 without diffusing the particular substance in the target space S. That is, the disinfecting and virus inactivating device 1 can send the particular substance in such a manner as to move the particular substrate toward positions where a large number of bacteria or viruses are present. Therefore, the disinfecting and virus inactivating device 1 can send the particular substance in a high concentration-state toward the movement locus 51 and efficiently perform bacteria disinfection or virus inactivation on bacteria or viruses that are present along the movement locus 51.

The disinfecting and virus inactivating device 1 can intensively inactivate bacteria or viruses at positions at which the person 50 comes into contact with respective objects or respective portions of an object, and can thus reduce the risk of contact transmission in the target space S. The disinfecting and virus inactivating device 1 is provided at a high position, such as on a ceiling, in the target space S, and can thus easily transmit a particular substance to a surface portion of the furniture 91 that the person 50 easily touches, as compared with the case where the disinfecting and virus inactivating device is provided on a surface of a floor.

During the disinfection/inactivation operation, the substance measuring module 34 measures the particular substance generated by the substance generating module 32. The substance measuring module 34 detects whether the particular substance is present or absent, and in the case where the particular substance is present, the substance measuring module 34 measures the concentration of the particular substance. When the controller 40 detects that the concentration of the particular substance measured by the substance measuring module 34 is less than or equal to a set concentration set in advance, the controller 40 stops the operation of the substance generating module 32, and activates the display module 36 such that the display module 36 is lit in a lighting state indicating that the amount of the generated particular substance is insufficient. With such an operation, the disinfecting and virus inactivating device 1 can make a notification indicating occurrence of abnormality.

Control Flowchart

Figure 9:
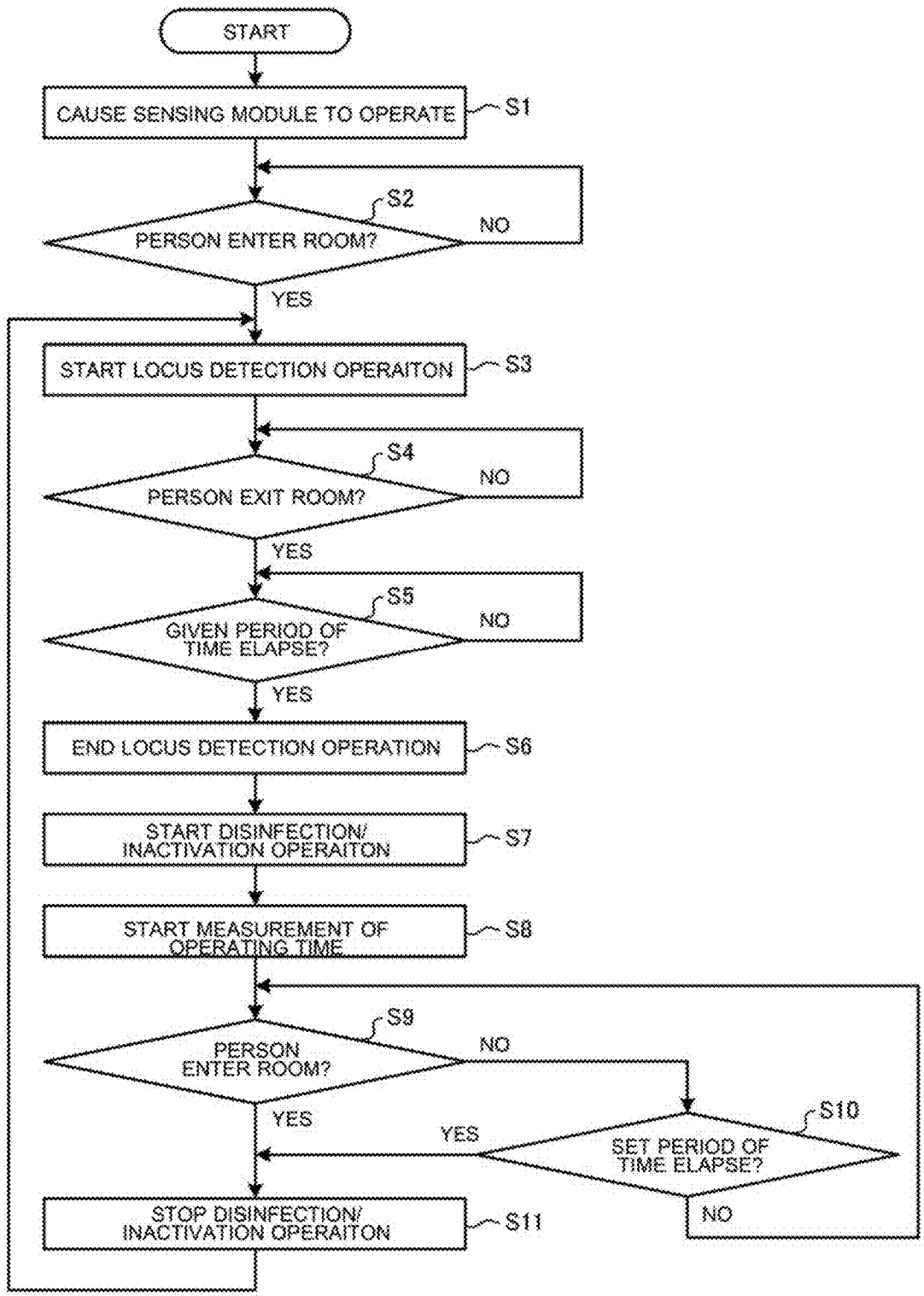
FIG. 9 is al flowchart of a control by the disinfecting and virus inactivating device according to Embodiment 1.

FIG. 9 is a flowchart of a control by the disinfecting and virus inactivating device 1 according to Embodiment 1. The control includes a locus detection step and a disinfection/inactivation step are present, and in the control, bacteria disinfection or virus inactivation in the target space S is performed. The flow of the control will be described with reference to the flowchart of FIG. 9.

When a remote switch (not illustrated) installed in the target space S is operated to turn on a power supply of the disinfecting and virus inactivating device 1, the controller 40 is started up and the sensing module 30 is activated (step S1). When the power supply is in an on-state, the sensing module 30 is in operation at all times to detect entry/exit of the person 50 into/from the target space S. The controller 40 is in operation at all times to detect entry/exit of the person 50 into/from the target space S on the basis of a sensing signal from the sensing module 30 (No in step S2). When the controller 40 detects entry of the person 50 (Yes in step S2), the controller 40 starts the locus detection operation by activating the locus detection module 31 (step S3). The locus detection module 31 continues detection of the movement locus 51 of the person 50 until the sensing module 30 detects exit of the person 50 (No in step S4).

When detecting exit of the person 50 from the target space S based on a sensing signal from the sensing module 30 (Yes in step S4), the controller 40 determines whether a predetermined time period elapses or not (step S5). When determining that the predetermined time period does not elapse (No in step S5), the controller 40 continues the locus detection operation. When determining that the predetermined time period elapses (Yes in step S5), the controller 40 ends the locus detection operation (step S6), and starts the disinfection/inactivation operation (step S7); that is, the controller 40 switches the operation from the locus detection operation to the disinfection/inactivation operation.

During the disinfection/inactivation operation, as described above, the controller 40 drives the substance generating module 32 to cause the substance generating module 32 to generate the particular substance, and starts the operation of the blower 37. Furthermore, the controller 40 starts measuring an operation time period simultaneously with the start of the disinfection/inactivation operation (step S8).

The disinfection/inactivation operation is performed for a set time period set in advance. However, when a person 50 enters the target space S before the set time period elapses, the disinfection/inactivation operation is stopped. Specifically, the controller 40 performs the following processing.

When the controller 40 does not detect entry of a person 50 after the disinfection/inactivation operation is started (No in step S9), the controller 40 determines whether the set time period elapses from the start of the measurement of the operation time period or not (step S10). When the set time period not elapse (No in step S10), the processing by the controller 40 returns to step S9 and the controller 40 repeats the process of step S9 and the process of step S10. When determining that the set time period elapses without detecting entry of a person 50 (Yes in step S10), the controller 40 stops the disinfection/inactivation operation (step S11). Furthermore, when the detecting entry of a person 50 during the disinfection/inactivation operation in step S9 (Yes in step S9), the controller 40 stops the disinfection/inactivation operation (step S11). That is, the controller 40 stops the driving of the substance generating module 32 to stop the generation of the particular substance, and stops the operation of the blower 37. After the disinfection/inactivation operation is stopped, the processing by the controller 40 returns to step S3, and the controller re-starts the locus detection operation.

The controller 40 is configured to switch the operation from the locus detection operation to the disinfection/inactivation operation after the predetermined time period elapses from the detection of exit of the person 50 from the target space S, for the following reason. If the controller 40 is configured to switch the operation from the locus detection operation to the disinfection/inactivation operation immediately after the detection of exit of the person 50, in the case where the person 50 frequently enters and exits the target space S, the operation is frequently switched. For this reason, the controller 40 is configured to switch the operation from the locus detection operation to the disinfection/inactivation operation after the predetermined time period elapses from the detection of exit of the person 50. With such a configuration, the disinfecting and virus inactivating device 1 can reduce the number of times the operation is switched, thus reducing a load that acts on the blower 37.

The disinfecting and virus inactivating device 1 includes the mode changing switch 41 to set a time lag of a predetermined time period. The mode changing switch 41 is a slide switch, provided at the connector 25, and prevented from being viewable from the outside. By removing the second casing 3 from the first casing 2, the user can operate the mode changing switch 41 through the upper opening of the first casing 2. In an initial state, the predetermined time period is a time period determined in advance. The user can change the predetermined time period by sliding the mode changing switch 41 to change the position thereof. For example, when the position of the mode changing switch 41 is changed to a first slide position, the predetermined time period is set to 30 seconds. When the position of the mode changing switch 41 is changed to a second slide position, the predetermined time period is set to 1 minute. The mode changing switch 41 is not limited to the slide switch.

As described above, the disinfecting and virus inactivating device 1 performs the disinfection/inactivation operation, when the person 50 exits the target space S and as a result, no person 50 is present in the target space S. Therefore, no problem arises even when the transmission module 33 is operated in such a manner as to obtain an air flow the amount of which corresponds to an amount of blowing air that is larger than or equal to a set amount of air that is necessary for ensuring comfort. In other words, no problem arises even when the transmission module 33 is operated in such a manner as to obtain an air flow the amount of which corresponds to an amount of blowing air that makes a noise or gives discomfort in an environment where the person 50 is present. Therefore, during the disinfection/inactivation operation, the transmission module 33 is operated in such a manner as to obtain an air flow the amount of which corresponds to an amount of blowing air that is larger than or equal to the set amount of air necessary for ensuring comfort, for example, in such a manner as to obtain an air flow corresponding to a maximum amount of blowing air. To be more specific, during the disinfection/inactivation operation, the blower 37 of the transmission module 33 is operated with an amount of blowing air that is larger than or equal to the set amount of air necessary for ensuring comfort, for example, with a maximum amount of blowing air. With such a configuration, the disinfecting and virus inactivating device 1 can effectively perform bacteria disinfection or virus inactivation. The amount of blowing air from the blower 37 during the disinfection/inactivation operation is not limited to the maximum amount of blowing air, and it suffices that the amount of blowing air is set such that bacteria disinfection or virus inactivation can be efficiently performed.

During the disinfection/inactivation operation, in the target space S, noise is made from the motor of the blower 37 and air flow having high straightness and high directivity is generated. Such an environment causes the person 50 to feel discomfort. However, the disinfecting and virus inactivating device 1 performs the disinfection/inactivation operation when no person 50 is present, and does not give discomfort to the person 50. Furthermore, since no person 50 is present in the target space S during the disinfection/inactivation operation, there is no possibility that an air flow having high straightness and high directivity will flow toward the person 50 from the disinfecting and virus inactivating device 1. Therefore, the disinfecting and virus inactivating device 1 can prevent the person 50 from feeling skin dryness or coldness. Accordingly, the disinfecting and virus inactivating device 1 can achieve an effective disinfection/inactivation operation that is considerate of the person 50.

It is described above that the controller 40 switches the operation from the locus detection operation to the disinfection/inactivation operation after the predetermined time period elapses from the stop of the locus detection operation. However, the controller 40 may switch the operation from the locus detection operation to the disinfection/inactivation operation when the concentration of the particular substance in the target space S decreases to a set concentration or less. In this case, when a substance having low persistence is used as the particular substance, the controller 40 can switch the operation from the locus detection operation to the disinfection/inactivation operation within a short time period.

The above description is made by referring to by way of example the case where only one person 50 enters the target space. However, in some cases, a plurality of persons 50 enter the target space. In this case, the disinfecting and virus inactivating device 1 performs the locus detection operation from time at which the first one of the plurality of persons 50 enters the target space to time at which all the plurality of persons 50 exit the target space, and performs the disinfection/inactivation operation after all the plurality of persons 50 exit the target space.

In Embodiment 1, ions are used as the particular substance. Ions are known as a substance having low persistence. In the case where the particular substance is a substance having low persistence, even when the concentration of the particular substance in the target space S reaches a high concentration during the disinfection/inactivation operation, by stopping the driving of the substance generating module 32, it is possible to rapidly decrease the concentration. Therefore, even when the particular substance is supplied into the target space S at a high concentration from the disinfecting and virus inactivating device 1 during the disinfection/inactivation operation, it is possible to ensure safety of the person 50 that enters the target space S after the disinfection/inactivation operation is performed. Accordingly, in the case where a substance having low persistence is used as the particular substance, the disinfecting and virus inactivating device 1 causes the substance generating module 32 to generate the particular substance such that the particular substance has a high concentration in the target space S. The high concentration in this case is not limited to a specific numerical value, and it suffices that the high concentration is set to a value that is effective for improvement of the efficiency of bacteria disinfection or virus inactivation.

As particular substances, not only ions but ozone is present. Ions and ozone differ from each other in persistence. Ozone has higher persistence than ions. Ozone has a relatively high persistence among particular substances. In the case where a substance having high persistence, such as ozone, is generated by the substance generating module 32, the disinfecting and virus inactivating device 1 generates the particular substance within a range in which the concentration of ozone in the target space S does not exceed a set concentration set in advance. This set concentration is the concentration of ozone that does not affect the human body, and is, for example, 0.05 ppm that is an environmental standard. With such a configuration, the disinfecting and virus inactivating device 1 can set the concentration of a substance having high persistence in the target space S to a value less than or equal to the environmental standard. Therefore, even in the case where the substance having high persistence is used as the particular substance, the disinfecting and virus inactivating device 1 can ensure safety of the person 50 who enters the target space S after the disinfection/inactivation operation is performed.

The particular substances also include a substance whose safety to the human body has not yet been clarified. However, the disinfecting and virus inactivating device 1 performs the disinfection/inactivation operation when no person is present, whereby there is no possibility that the person will inhale or touch the particular substance. Accordingly, the disinfecting and virus inactivating device 1 can achieve an effective disinfection/inactivation operation that is safe for persons.

Advantage

As described above, the disinfecting and virus inactivating device 1 of Embodiment 1 includes the locus detection module 31 configured to detect the movement locus of locations where the moving body comes into contact with respective objects or respective portions of an object in the target space S, the substance generating module 32 configured to generate the particular substance for use in disinfection treatment or inactivation treatment, and the transmission module 33 configured to generate an air flow and transmit the particular substance generated by the substance generating module to the movement locus.

In such a manner, the disinfecting and virus inactivating device 1 transmits the particular substance to the movement locus 51 of locations where the moving body comes into contact with respective objects or respective portions of an object in the target space S, whereby it is possible to efficiently perform disinfection or virus inactivation in the target space S.

The transmission module 33 includes the blower 37, the grille 4a, and the driving device 39. The blower 37 is configured to generate an air flow. The grille 4a is provided downstream of the blower 37 and configured to give straightness and directivity to the air flow from the blower 37. The driving device 39 is configured to control the blowing direction of the air flow by changing the orientation of the grille 4a. The transmission module 33 transmits the airflow in such a manner as to cause the air flow to trace the movement locus 51 by changing the orientation of the grille 4a by the driving device 39.

In such a manner, the disinfecting and virus inactivating device 1 transmits the air flow to which straightness and directivity are given by the grille 4a such that the air flow traces the movement locus 51, whereby it is possible to intensively perform disinfection or virus inactivation on a location at which the risk of infection is high.

The disinfecting and virus inactivating device 1 further includes the sensing module 30 configured to detect exit of the moving body from the target space S. When the sensing module 30 detects that the moving body exits the target space S, the transmission module 33 transmits the particular substance generated by the substance generating module 32 to locations through which the movement locus is described.

In such a manner, when it is detected that the moving body exits the target space S, the disinfecting and virus inactivating device 1 drives the substance generating module 32 and the transmission module 33 to start transmission of the particular substance to locations through which the movement locus is described, that is, to start the disinfection/inactivation operation, whereby it is possible to intensively perform disinfection or virus inactivation while no moving body is present in the target space S. In other words, the disinfecting and virus inactivating device 1 does not perform the disinfection/inactivation operation while a moving body is present in the target space S, and can thus effectively perform the disinfection/inactivation operation while ensuring comfort for the moving body in the target space S.

When the sensing module 30 detects that the moving body exits the target space S, the transmission module 33 transmits the particular substance generated by the substance generating module 32 to locations through which the movement locus is described, after the elapse of the predetermined time period set in advance.

With such a configuration, the disinfecting and virus inactivating device 1 can reduce the number of times the operation is switched in the case where a moving body frequently enters or exits the target space S, thereby reducing a load that acts on the blower 37. Furthermore, the disinfecting and virus inactivating device 1 can prevent the moving body from feeling discomfort in terms of noise and coolness, for example, when the moving body that exits the target space S immediately returns to the target space S.

Modification

The control and configuration of the infecting and virus inactivating device 1 according to the present disclosure is not limited to such a control and a configuration as described above, and may be modified as follows, for example, without departing from the gist of the present disclosure.

Modification of Control

Figure 10:
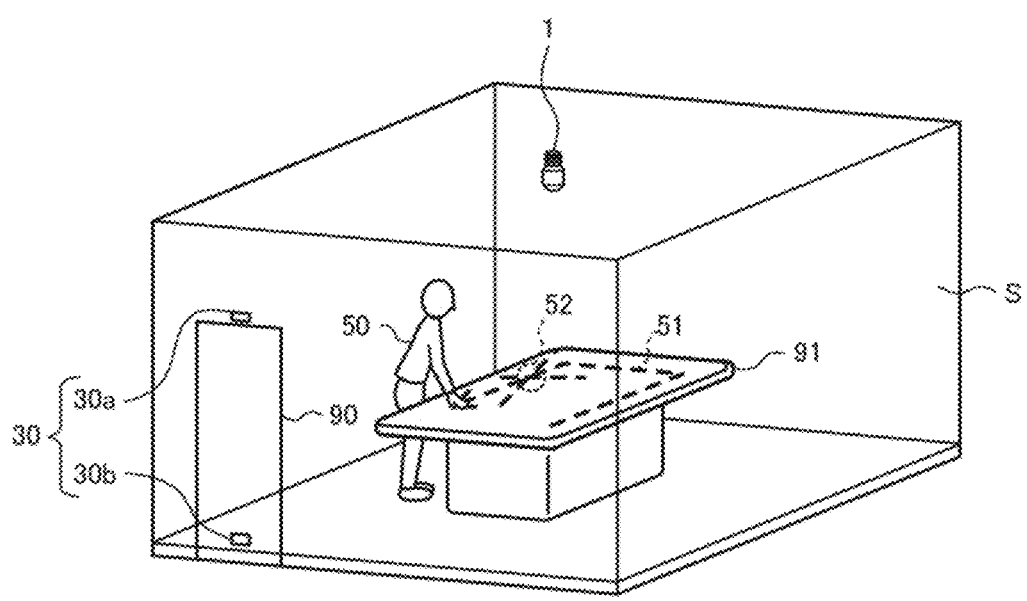
FIG. 10 is an explanatory view for a modification of the control by the disinfecting and virus inactivating device according to Embodiment 1.
Figure 11:
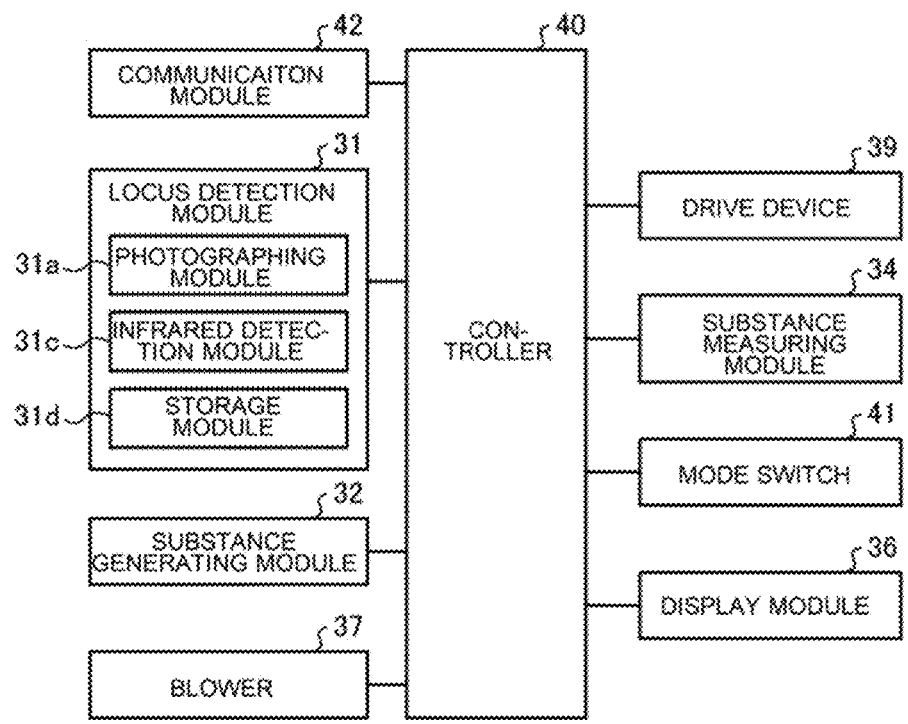
FIG. 11 is a block diagram of a disinfecting and virus inactivating device according to Embodiment 2.

FIG. 10 is an explanatory view for a modification of the control by the disinfecting and virus inactivating device 1 according to Embodiment 1.

The person 50 moves in various ways in the target space S, and there are locations at which a plurality of movement loci 51 overlap with each other. A locus overlapping region 52 where the plurality of movement loci 51 overlap with each other is a location where the person 50 repeatedly comes into contact with an object, and at the locus overlapping region 52, there is a possibility that a large amount of germ or viruses may exist, as compared with other locations. For this reason, the disinfecting and virus inactivating device 1 may perform an operation for enhancing the disinfection/inactivation effect against germ or viruses that are present at the locus overlapping region 52.

Operations of enhancing the disinfection/inactivation effect includes an operation of increasing the amount of a blowing air, an operation of increasing the amount of the particular substance to be generated, and an operation of increasing a time period in which the particular substance is transmitted, for example. The disinfecting and virus inactivating device 1 performs the operation of enhancing the disinfection/inactivation effect by performing some or all of those three operations. That is, either one or both of the substance generating module 32 and the transmission module 33 perform some or all of the above three operations as the operation of enhancing the disinfection/inactivation effect. Specific control is as follows. The controller 40 performs some or all of the above three operations by controlling either one or both of the substance generating module 32 and the transmission module 33 as follows.

The controller 40 increases the blowing amount by increasing the rotation speed of the blower 37 of the transmission module 33. In the case where the substance generating module 32 is an ion generating device, the controller 40 increases a voltage that is applied to an electrode. By increasing a voltage that is applied to the electrode increases, it is possible to increase the number of ions that are generated by the substance generating module 32, and thus increase the amount of the particular substance to be transmitted to the locus overlapping region 52.

In order to increase the time required to transmit the particular substance toward the locus overlapping region 52, it suffices that the controller 40 performs the following control, for example. In the case of transmitting the particular substance in such a manner as to cause the particular substance to trace the movement locus 51, while changing the orientation of the grille 4a by driving the first casing 2, it suffices that the controller 40 changes the orientation of the grille 4a for the locus overlapping region 52 at a speed lower than for a non-locus overlapping region.

Modification of Configuration

Although a propeller fan is adopted as the transmission module 33 by way of example in Embodiment 1, a sirocco fan may be adopted. The sirocco fan can blow a large amount of air at a static pressure, thus enabling bacteria disinfection or virus inactivation to be effectively performed.

Although it is described above that in the above configuration, the sensing module 30 provided separately from the housing 1a detects entry/exit of the moving body into/from the target space S, the locus detection module 31 may double as the sensing module 30. In the case where the locus detection module 31 doubles as the sensing module 30, the locus detection module 31 can detect entry/exit of a person 50 into/from the target space S that is detected by the sensing module 30 in the above configuration, by performing the following processing.

The locus detection module 31 performs image difference processing to form a difference image between background data on the door 90 in the target space S and current image data obtained by photographing the door 90. When detecting, in the difference image obtained by the image difference processing, a difference in luminance value in the image of the door 90 in the target space S, the locus detection module 31 can detect it as entry/exit of the person 50 into/from the target space S. Furthermore, the locus detection module 31 can detect entry/exit of the person 50 into/from the target space S as follows: when a change in the difference image is made toward the inside of the target space S, the locus detection module 31 detects entry of the person 50 into the target space S, and when the change in the difference image is made toward the outside of the target space S, the locus detection module 31 detects exit of the person 50 from the target space S.

In the case of adopting the configuration in which the locus detection module 31 doubles as the sensing module 30, the locus detection module 31 may include a visible light sensor or an ultrasonic sensor and detect the movement locus 51 of the moving body based on the result of detection by the sensor.

Although it is described above that in the above configuration, the target space S is a closed space partitioned off by partitions, for example, it is allowable that the target space S is not closed. The space not closed corresponds to, for example, a space defined by virtually partitioning off part of a large space, such as a banquet hall. In the case of using the space not closed as the target space S, the disinfecting and virus inactivating device 1 assumes part of a large space as the target space S, without forming a closed space by physically partitioning off the large space, for example, and can then perform the disinfection/inactivation operation. In such a manner, in the case where the space not closed is used as the target space S, the disinfecting and virus inactivating device 1 is installed at a position where the particular substance generated by the substance generating module 32 can be transmitted to the target space S by the transmission module 33.

It order to detect entry/exit of the moving body into/from the space not closed, it suffices that an imaginary border of the space not closed is set, and monitoring is performed to detect entry/exit of the moving body through the entire border. To be more specific, it suffices to adopt a configuration in which a plurality of sensing modules 30 are provided at respective positions on the border to detect entry/exit of the moving body into/from the space through each of the positions on the border. When it is detected that the moving body enters the space, the locus detection module 31 detects the locus of the moving body until the moving body exits the space. After the sensing modules 30 confirm that the moving body exits the space, the disinfecting and virus inactivating device 1 performs the disinfection/inactivation operation. In such a manner, since the sensing modules 30 are provided for the entire border of the target space S, the disinfecting and virus inactivating device 1 can perform bacteria disinfection or virus inactivation on a space that is not partitioned off.

Although it is described above that in the above configuration, the locus detection module 31 is provided at the central portion of the lower end of the grille body 4, the position at which the locus detection module 31 is provided is not limited to a position in the housing 1a, and the locus detection module 31 may be provided on the outer wall of the housing 1a or at a position located apart from the housing 1a. In short, the locus detection module 31 may be provided at a position where the locus detection module 31 can easily detect the locus of the moving body, on the basis of, for example, the arrangement of the furniture 91 in the target space S.

Although it is described above that in the above configuration, the substance generating module 32 is provided upstream of the blower 37, the substance generating module 32 may be provided downstream of the blower 37. With such a configuration, the disinfecting and virus inactivating device 1 is configured such that the particular substance generated by the substance generating module 32 does not pass through the blower 37, and it is therefore possible to prevent deterioration of the blower 37 that would be caused by the particular substance.

In the above configuration, the first casing 2 to which the grille body 4 is attached and the second casing 3 including the driving device 39 that drives the first casing 2 are provided as separate members, and the grille 4a of the grille body 4 is made to face the movement locus 51 by changing the shape of the second casing 3. However, the disinfecting and virus inactivating device 1 may be formed as, for example, an integral type disinfecting and virus inactivating device in which the grille body 4 itself is driven, for example. In the case of adopting such a configuration, it is possible to reduce the number of components and thus produce the disinfecting and virus inactivating device 1 at a low cost.

In the above configuration, a coaxial double cylindrical ion sensor is adopted as the ion sensor included in the substance measuring module 34. However, a parallel-plate ion sensor may be adopted as the ion sensor. The parallel-plate type ion sensor measures the number of ions that flow between flat plate electrodes provided in parallel, from the amount of current between the flat plate electrodes. The parallel-plate ion sensor is made compact and can simply measure the number of ions.

In the above configuration, the first storage module that stores background data is formed separate from the second storage module that stores tracking data. However, the background data and the tracking data may be stored in a single storage module. In this case, it is possible to reduce the number of components of the disinfecting and virus inactivating device 1, thus achieving a simple configuration.

The disinfecting and virus inactivating device 1 may be configured such that the amount of generation of a substance or the amount of air can be changed in response to an instruction concerning settings that is input by the user. In the case where the target space S is a space that one person exits and then another person enters for a short time period, the operation time of the disinfection/inactivation operation tends to be short. In this case, the user sets the amount of generation of the substance or the amount of air such that the amount is increased larger than in a default normal setting. As a result, the disinfecting and virus inactivating device 1 can more promptly perform bacteria disinfection or virus inactivation than in the case where control is performed based on the normal setting.

The above setting may be made by the user, or may be automatically made by the disinfecting and virus inactivating device 1. In the case where the setting is automatically made by the disinfecting and virus inactivating device 1, it suffices that the number of times a person or persons enter the space or exit the space in a day is counted, and when a count value is larger than the threshold set in advance, the setting is changed such that the amount of generation of the substance or the amount of air is larger than that in the normal setting.

In the case where it is considered necessary to take measures at a higher level than usual because viruses mutate and seriously affect human bodies, as in the case where new coronavirus infectious diseases spread, the user makes a setting of increasing the amount of generation of the substance or the amount of air, as compared with that in the default normal setting. By making such a setting, it is possible to enhance the disinfection/inactivation effect and thus enhance the infection preventing effect.

In the above configuration, the mode changing switch 41 is provided at the connector 25, and is not viewable from the outside. However, the mode changing switch 41 may be provided at an outer portion of the first casing 2 such that it is viewable from the outside. In this case, the user can easily operate the mode changing switch 41 and can thus easily change the time lag.

Embodiment 2

Embodiment 2 is different from Embodiment 1 in the configuration of the locus detection module 31. In Embodiment 2, the other configurations are the same as or equivalent to those in Embodiment 1. The following description is made by referring mainly to the differences in configuration between Embodiments 1 and 2. Components that will not be described regarding Embodiment 2 are substantially the same as those in Embodiment 1.

Microorganisms are more frequently brought into the target space S by moving bodies that generate heat and include organisms, such as humans, dogs, and cats than by moving bodies that do not generate heat, such as mobile machines or devices. That is, it can be said that of moving bodies that are present in the target space S, a moving body that generates heat increases the risk of contact transmission to a high level at locations on the movement locus of the moving body. Thus, in order to efficiently perform bacteria disinfection or virus inactivation in the target space S, it is preferable that the particular substance be transmitted toward the movement locus 51 of the moving body that generates heat. Therefore, the disinfecting and virus inactivating device 1 according to Embodiment 2 detects the movement locus 51 of a moving body that generates heat, among moving bodies in the target space S, using the locus detection module 31, and transmits the particular substance to the movement locus 51 of the detected moving body to efficiently perform disinfection or inactivation on objects or portions of an object that are situated on locations on the locus where the risk of contact transmission is high.

In the disinfecting and virus inactivating device 1 of Embodiment 2, the locus detection module 31 doubles as the sensing module 30. Accordingly, in the disinfecting and virus inactivating device 1 of Embodiment 2, the sensing module 30 provided separately from the housing 1*a* is omitted.

FIG. 11 is a block diagram of the disinfecting and virus inactivating device 1 according to Embodiment 2. The locus detection module 31 of the disinfecting and virus inactivating device 1 according to Embodiment 2 includes a photographing module 31*a*, an infrared-ray detection module 31*c*, and a storage module 31*d*. The locus detection module 31 detects the movement locus 51 of a moving body in the target space S from the result of detection by the infrared-ray detection module 31*c*.

The photographing module 31*a* photographs the target space S in the same manner as in Embodiment 1. The infrared-ray detection module 31*c* detects infrared rays emitted from a heat source, such as a person. The infrared-ray detection module 31*c* is a pyroelectric sensor, for example. Although not illustrated, the pyroelectric sensor includes a sensor module, a movable module, and a signal processing circuit module. The sensor module includes a plurality of pyroelectric elements arranged in a column in a vertical direction. The movable module rotates the sensor module in a lateral direction. The signal processing circuit module processes a signal obtained by the sensor module. The pyroelectric sensor scans the target space S by causing the movable module to rotate the sensor module, and divides the target space S into a plurality of regions to be subjected to measurement. The pyroelectric sensor detects which of the regions is a region where the moving body is present, from the result of the above measurement.

Although not illustrated, the signal processing circuit module of the pyroelectric sensor includes an amplifier circuit, a band pass filter, a comparator circuit, and an output circuit. The amplifier circuit amplifies a signal from the pyroelectric element. The band pass filter removes unnecessary frequency components that become noises, from the amplified signal. The comparator circuit determines whether the signal from which the unnecessary frequency components are removed is higher in value than the threshold set in advance, and the comparator circuit outputs a signal indicating the result of the determination to the output circuit. When the signal from the comparator circuit indicates a value higher than the threshold, the output circuit outputs a detection signal indicating detection of a moving body. That is, the signal processing circuit module amplifies a signal from the pyroelectric element and compares the signal with the threshold to detect a region associated with part of the signal that has a value higher than the threshold, as a region where the moving body is present.

The storage module 31*d* of the locus detection module 31 stores the location of a moving body that is detected by the infrared-ray detection module 31*c*, on image data obtained by photographing of the target space S that is performed by the photographing module 31*a* when no moving body is present in the target space S. The locus detection module 31 can detect the movement locus 51 of the moving body by accumulating data on detected locations of the moving body that are obtained with the passage of time. In order to store image data having a large amount of data, a large capacity storage device is used as the storage module 31*d*. For example, a volatile memory having a relatively large storage capacity, such as a dynamic random access memory (DRAM), can be used as the storage module 31*d*.

In the above configuration, the locus detection module 31 is configured to detect the movement locus 51 of a moving body that generates heat in the target space S. Therefore, when a moving body that does not generate heat, such as a movable toy or a movable cleaning robot, moves in the target space S, the locus detection module 31 does not recognize such a moving body as a detection target, and does not detect the movement locus 51 of the moving body. That is, the locus detection module 31 detects, as a detection target, only a moving body that generates heat. Therefore, the disinfecting and virus inactivating device 1 can intensively transmit the particular substance to locations where the risk of contact transmission is high in the target space S, and can thus efficiently perform bacteria disinfection or virus inactivation in the target space S.

According to Embodiment 2, it is possible to obtain advantages that are the same as those obtained in Embodiment 1, and the locus detection module 31 includes the infrared-ray detection module 31*c* to detect the movement locus 51 of a moving body that generates heat and that is highly likely to carry microorganisms into the target space S. It is therefore possible to further obtain the following advantage. The disinfecting and virus inactivating device 1 of Embodiment 2 can intensively transmit the particular substance to locations where the risk of contact transmission is high in the target space S, and can thus efficiently perform bacteria disinfection or virus inactivation in the target space S.

Modification

Next, a modification of Embodiment 2 will be described. The following description is made by referring mainly to the differences between the modification and the contents of the above configurations, and matters that will not be described regarding the modification are the same as those in the above descriptions.

When a person is infected with bacteria or viruses and develops a disease, such as a cold, his or her body temperature rises. A person having a higher body temperature carries a larger number of bacteria, and a large number of bacteria or viruses adheres to the furniture 91 with which the person having a high body temperature comes into contact. Thus, the disinfecting and virus inactivating device 1 of the modification preferentially performs inactivation on a location where the risk of transmission is high, that is, an object with which the moving body having a high body temperature comes into contact, among locations where persons come into contact with respective objects or respective portions of an object.

The disinfecting and virus inactivating device 1 has a plurality of thresholds based on which the temperatures of persons that are moving bodies are classified into a plurality of temperature zones, such as a low temperature zone, an intermediate temperature zone, and a high temperature zone. In the case where the plurality of thresholds are, for example, 37 degrees C. and 38.5 degrees C., the temperatures of persons are classified into three temperature zones: that is, a low temperature zone from 37 degrees C. to less than 37 degrees C., an intermediate temperature zone from 37 degrees C. to 38.5 degrees C., and a high temperature zone from 38.5 degrees C. or more than 38.5 degrees C. The above number of classifications and temperature values of the temperature zones are described as examples, and are not limited to the above number and values.

Figure 12:
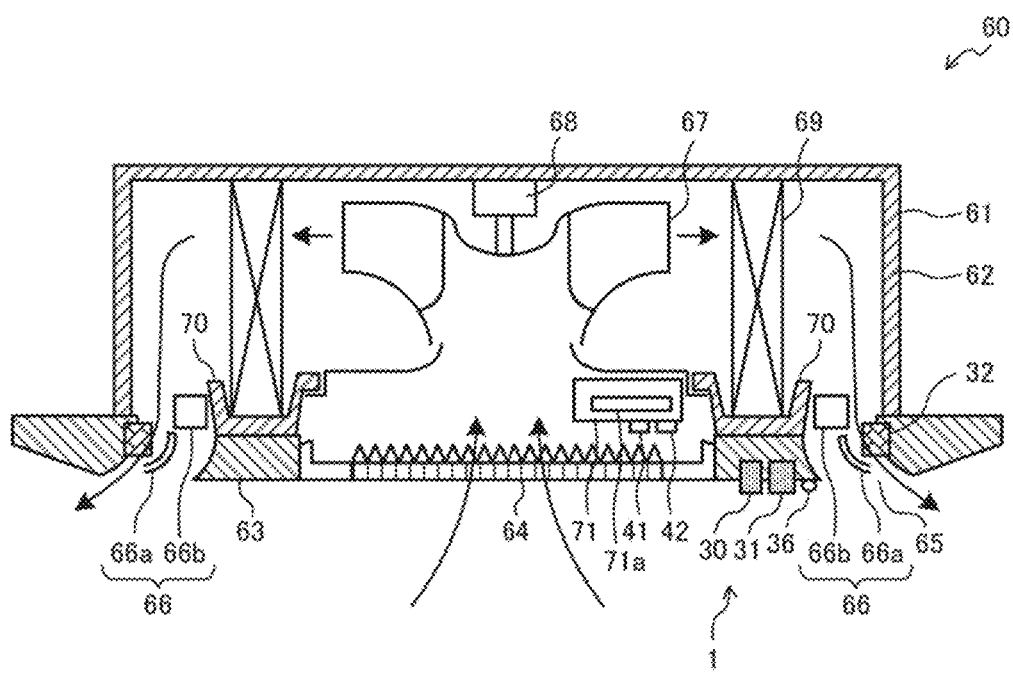
FIG. 12 is a schematic sectional view of an air-conditioning apparatus according to Embodiment 3.
Figure 13:
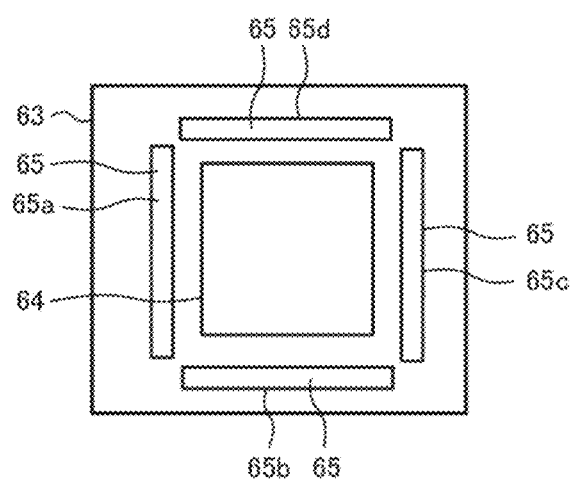
FIG. 13 is a schematic view of the air-conditioning apparatus 60 as illustrated in FIG. 12, as viewed from below.

The disinfecting and virus inactivating device 1 transmits an air flow containing the particular substance to a plurality of movement loci 51 in turn. Based on the result of classification of the temperatures of persons into temperature zones that are detected by the locus detection module 31, the disinfecting and virus inactivating device 1 transmits the air flow containing the particular substance to the plurality of movement loci 51 in turn from the movement locus 51 of a person whose temperature falls within the high temperature zone to the movement locus 51 of a person whose temperature falls within the low temperature zone. That is, in the case where a person whose temperature falls within the high temperature zone, a person whose temperature falls within the intermediate temperature zone, and a person whose temperature falls within the low temperature zone are detected, the disinfecting and virus inactivating device 1 performs the following operation: first, the disinfecting and virus inactivating device 1 operates to transmit the particular substance toward the movement locus 51 of the person whose temperature falls within the high temperature zone, and then, operates to transmit the particular substance toward the movement locus 51 of the person whose temperature falls within the intermediate temperature zone, and thereafter, operates to transmit the particular substance toward the movement locus 51 of the person whose temperature falls within the low temperature zone.

The disinfecting and virus inactivating device 1 also operates to enhance the disinfection/inactivation effect on the movement loci 51 in turn from the movement locus 51 of the person whose temperature falls within the low temperature zone to the movement locus 51 of the person whose temperature falls within the high temperature zone. In the same manner as the operation performed on the locus overlapping region 52 in Embodiment 1, the operations of enhancing the disinfection/inactivation effect, for example are an operation of increasing a blowing amount, an operation of increasing the amount of generation of the particular substance, and an operation of increasing the time for which the particular substance is transmitted. To be more specific, for example, the blowing amount for the movement locus 51 of the person whose temperature falls within the intermediate temperature zone is set larger than that for the movement locus 51 of the person whose temperature falls within the low temperature zone, and the blowing amount for the movement locus 51 of the person whose temperature falls within the high temperature zone is set far larger than that for the movement locus 51 of the person whose temperature falls within the intermediate temperature zone.

Unlike the related art, the disinfecting and virus inactivating device 1 having the above configuration can obtain the following remarkable advantage. Of bacteria or viruses on the movement loci 51 of moving bodies, particularly, bacteria or viruses on the movement locus 51 of a moving body whose temperature zone falls within the high temperature zone and of locations where the risk of transmission is high can be preferentially subjected to disinfection or inactivation.

In the disinfecting and virus inactivating device 1 of Embodiment 2, the pyroelectric sensor is adopted as the infrared-ray detection module 31*c* of the locus detection module 31, but an infrared ray camera may be adopted as the infrared-ray detection module 31*c*. In the case where the infrared ray camera is adopted as the locus detection module 31, it is possible to quickly switch the operation between the locus detection operation and the disinfection/inactivation operation for the following reason. In the case where the pyroelectric sensor is adopted as the infrared-ray detection module 31*c*, the locus detection module 31 performs locus detection processing after all temperature information on respective areas is obtained. In contrast, in the case where the infrared ray camera is adopted as the infrared-ray detection module 31*c*, the locus detection module 31 can perform the locus detection processing immediately after photographing is performed to obtain one image, thereby increasing the processing speed. Accordingly, in a configuration in which the infrared ray camera is adopted as the locus detection module 31, it is possible to shorten the time required for the locus detection processing.

The disinfection/inactivation operation requires information on the movement locus 51 obtained by the locus detection operation. Inevitably, the disinfection/inactivation operation cannot be started until the locus detection processing is completed. Therefore, when it takes time to complete the locus detection processing, the disinfection/inactivation operation cannot be started at a timing at which the disinfection/inactivation operation should be started after the moving body exists the target space S. In the case where the infrared ray camera is adopted as the locus detection module 31, as described above, the time required for the locus detection processing can be reduced, whereby it is possible to quickly switch the operation from the locus detection operation to the disinfection/inactivation operation.

The modification of Embodiment 2 is descried above. However, the modification of Embodiment 1 is applicable to the disinfecting and virus inactivating device 1 of Embodiment 2 as appropriate. To be more specific, the operation of enhancing the disinfection/inactivation effect that is performed on the locus overlapping region 52, which is described above as the modification of Embodiment 1, is applicable to the disinfecting and virus inactivating device 1 of Embodiment 2.

Embodiment 3

Embodiment 3 relates to an air-conditioning apparatus 60 that includes the disinfecting and virus inactivating device 1 of Embodiment 1 or Embodiment 2. The following description is made by referring mainly to components and processing in Embodiment 3 that are different from those of Embodiment 1 or Embodiment 2, and components and processing that will not be described regarding Embodiment 3 are the same as those in Embodiment 1 or Embodiment 2.

FIG. 12 is a schematic sectional view of the air-conditioning apparatus 60 according to Embodiment 3. FIG. 13 is a schematic view of the air-conditioning apparatus 60 as illustrated in FIG. 12, as viewed from below. The air-conditioning apparatus 60 is an indoor unit that is installed in an air-conditioning target space, such as an office, and the air-conditioning apparatus 60 supplies conditioned air into the air-conditioning target space by utilizing a refrigeration cycle in which refrigerant is circulated. The air-conditioning apparatus 60 performs either one or both of a heating operation and a cooling operation as a normal operation. The air-conditioning apparatus 60 conditions air in the air-conditioning target space, and includes the disinfecting and virus inactivating device 1 of Embodiment 1 or Embodiment 2 to perform bacteria disinfection or virus inactivation on the air-conditioning target space, which is the target space S.

A housing 61 of the air-conditioning apparatus 60 includes a main body 62 and a decorated panel 63. The main body 62 is embedded in a ceiling and having an opening on its lower side. The decorated panel 63 closes the opening of the main body 62. The decorated panel 63 includes a suction grille 64 having a rectangular shape and located at a central portion of the decorated panel 63. Four air outlets 65 (65a to 65d) are formed around the suction grille 64 along four sides of the suction grille 64. At the air outlets 65, respective air direction plates 66 are provided. Each of the air direction plates 66 controls the blowing direction of an air flow from an associated one of the air outlets 65. In the air-conditioning apparatus 60, each air direction plate 66 includes a vertical air direction plate 66a and a lateral air direction plate 66b. The vertical air direction plate 66a controls the flow direction of air in the vertical direction, the lateral air direction plate 66b controls the flow direction of air in the lateral direction. Furthermore, in the housing 61, motors (not illustrated) are provided as driving devices that drive the vertical air direction plate 66a and the lateral air direction plate 66b.

In the housing 61, a centrifugal blower 67, a motor 68, and a heat exchanger 69 are provided. The motor 68 drives the centrifugal blower 67. The heat exchanger 69 causes heat exchange to be performed between air and refrigerant that flows in the heat exchanger 69. The centrifugal blower 67 is provided in a central region in the housing 61, and is connected to a shaft that extends downward from the motor 68 fixed to a top plate of the housing 61. The heat exchanger 69 is provided around the centrifugal blower 67. Furthermore, in the housing 61, a drain pan 70 is provided under the heat exchanger 69, and receives condensation water generated in the heat exchanger 69. In addition, in the housing 61, an electric component box 71 is provided. The electric component box 71 houses a control board 71a that controls the operation of the air-conditioning apparatus 60. It should be noted that FIG. 12 illustrates an example in which the air-conditioning apparatus 60 is a ceiling suspended indoor unit. However, the air-conditioning apparatus 60 is not limited to the ceiling suspended indoor unit and may be a wall-mounted indoor unit.

The air-conditioning apparatus 60 includes the disinfecting and virus inactivating device 1 of Embodiment 2. To be more specific, the sensing module 30 and the locus detection module 31 are provided at the decorated panel 63, and the substance generating module 32 is provided close to each air outlet 65 of the decorated panel 63. The transmission module 33 includes the centrifugal blower 67, the air direction plates 66, and the motors (not illustrated) that drive the air direction plates 66. The centrifugal blower 67 doubles as the blower 37 of the transmission module 33. Each air direction plate 66 has a function of the grille 4a of the transmission module 33. The display module 36 is provided on an outer surface of the decorated panel 63. The mode changing switch 41 and the communication module 42 are installed on an outer surface of the electric component box 71. The control board 71a in the electric component box 71 has the function of the controller 40.

Figure 14:
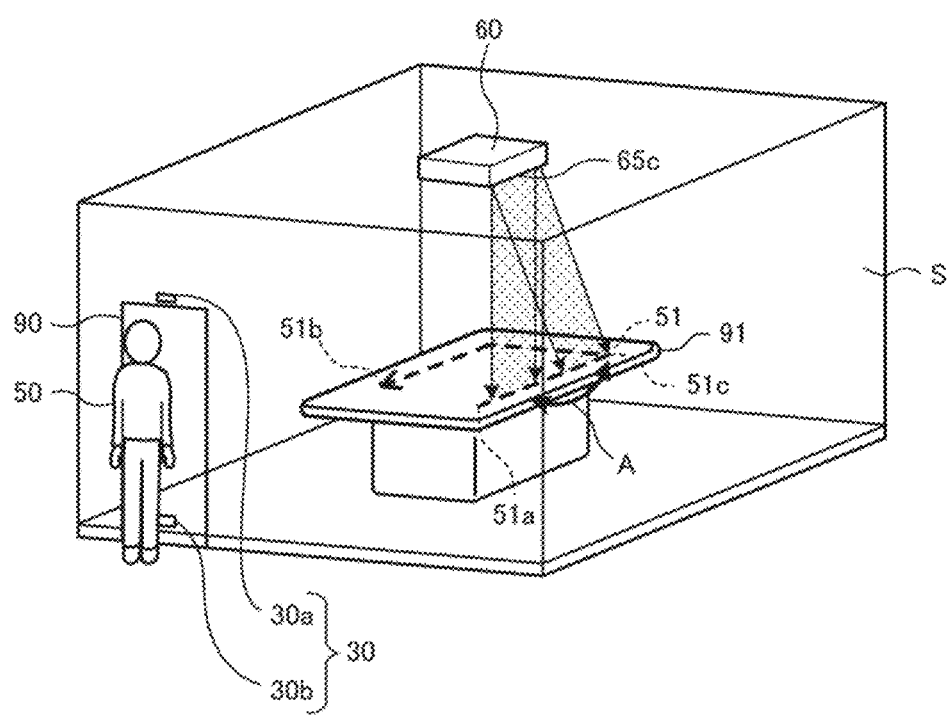
FIG. 14 is an explanatory view for a disinfection/inactivation operation by the air-conditioning apparatus 60 as illustrated in FIG. 12.

FIG. 14 is an explanatory view for the disinfection/inactivation operation by the air-conditioning apparatus 60 as illustrated in FIG. 12.

The air-conditioning apparatus 60 is installed at a position at which the air-conditioning apparatus 60 can transmit an air flow toward the furniture 91. In practice, in many cases, the air-conditioning apparatus 60 is installed in a room prior to installation of the furniture 91. Thus, the furniture 91 is installed at a position at which an air flow from the air-conditioning apparatus 60 reaches the furniture 91. Alternatively, the air-conditioning apparatus 60 may be installed based on the layout of the installed furniture 91 in the target space S at the time of installing the air-conditioning apparatus 60. In any case, the air-conditioning apparatus 60 is installed such that the movement locus of locations where a person comes into contact with respective objects or respective portions of an object is located within a region in which an air flow from the air-conditioning apparatus 60 is blown.

In the air-conditioning apparatus 60, when the centrifugal blower 67 is rotated by the motor 68, air is sucked into the housing 61 through the suction grille 64, passes through the centrifugal blower 67 and the heat exchanger 69, and is then blown out from the air outlets 65. An airflow blown out from the air outlets 65 is an airflow that is conditioned in temperature by the heat exchanger 69 and that contains the particular substance generated by the substance generating module 32. Such an air flow is blown out from the air outlets 65, and the blowing direction of the air flow is controlled by the air direction plates 66.

FIG. 14 illustrates a state in which an air flow is transmitted from the air outlet 65c to the movement locus 51. In more detail, FIG. 14 illustrates a state in which an air flow is transmitted from the air outlet 65c in such a manner as to trace an area between the start point 51a and a pass point 51c of the movement locus 51 in directions indicated by arrows A. After the transmission of the air flow from the air outlet 65c ends, an air flow is transmitted from the air outlet 65b and the air outlet 65a in turn toward the remaining part of the movement locus 51. In the air-conditioning apparatus 60, the blowing direction of the air flow is controlled by the air direction plates 66, whereby it is possible to transmit an air flow having high straightness and high directivity toward the movement locus 51 of a person in the air-conditioning target space.

Figure 15:
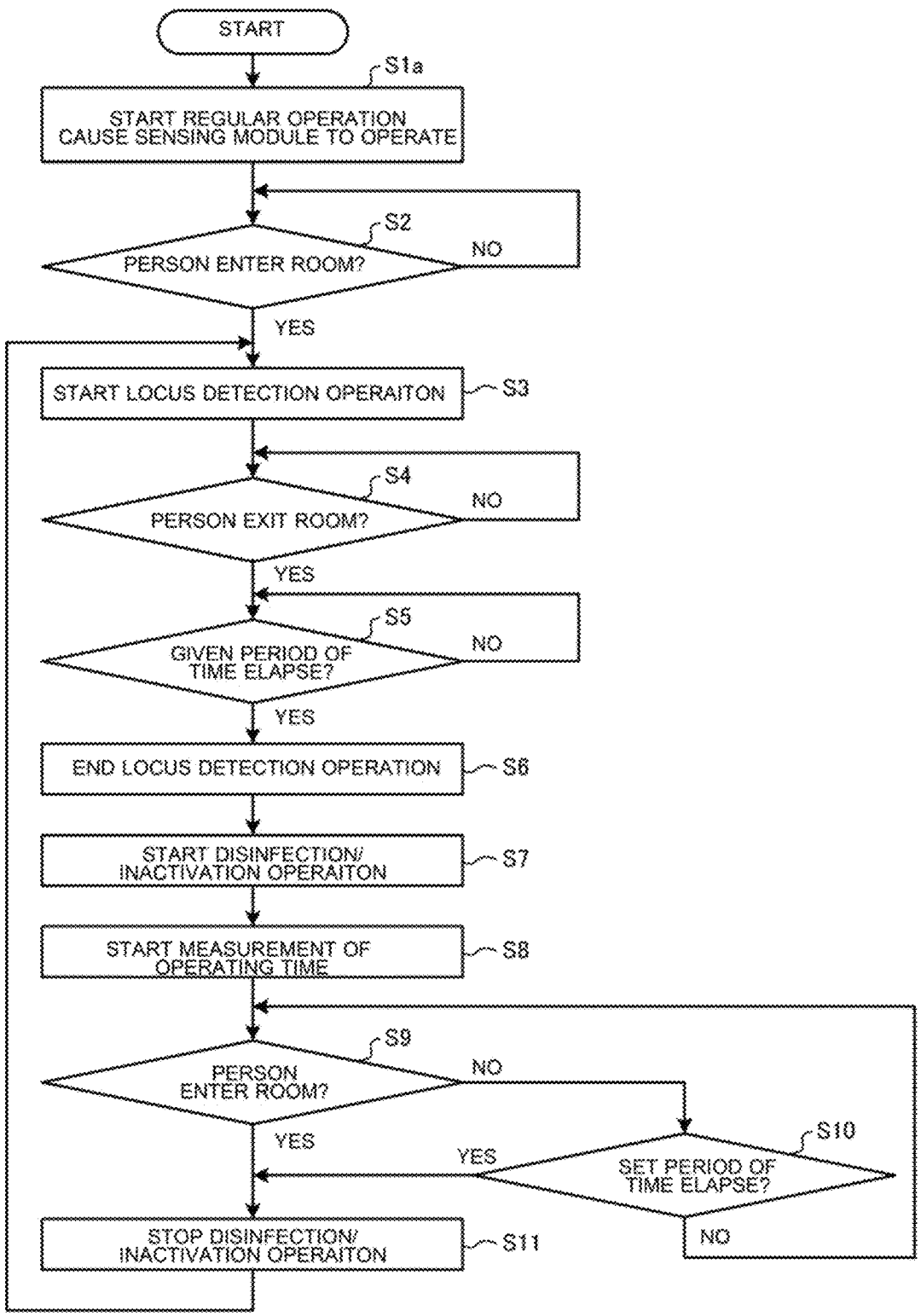
FIG. 15 is an operation flowchart of the air-conditioning apparatus according to Embodiment 3.

FIG. 15 is an operation flowchart of the air-conditioning apparatus 60 according to Embodiment 3. An operation flow of the air-conditioning apparatus 60 will be described with reference to the flowchart of FIG. 15. The following description is made by referring mainly to the differences between the flowchart of FIG. 15 and that of FIG. 9 relating to Embodiment 1.

When a remote switch (not illustrated) installed in the target space S is operated to turn on the power supply of the disinfecting and virus inactivating device 1, the controller 40 is started up to start a normal operation, and the sensing module 30 is activated (step S1a). The normal operation is an operation set by a remote control (not illustrated), and is, for example, the heating operation or the cooling operation. The following operations from the above operation onward are the same as the corresponding operations indicated in FIG. 9. That is, according to the flowchart of the operation of the air-conditioning apparatus 60, when the power is turned on, the air-conditioning apparatus 60 starts the normal operation. On this point, the flowchart of the operation of the air-conditioning apparatus 60 is different from the flowchart indicated in FIG. 9. On the other points, the flowchart of the operation of the air-conditioning apparatus 60 is the same as the flowchart indicated in FIG. 9.

The air-conditioning apparatus 60 of Embodiment 3 can obtain the same advantages as in Embodiments 1 and 2, and further obtain the following advantages. In Embodiment 3, an existing air-conditioning apparatus 60 originally installed in the air-conditioning target space, such as an office, is modified to have a configuration in which a constituting unit that forms the disinfecting and virus inactivating device 1 is incorporated into the air-conditioning apparatus 60 as appropriate. Therefore, in Embodiment 3, it is possible to efficiently perform disinfection or virus inactivation in the air-conditioning target space without changing the appearance of the air-conditioning target space. In the case where the existing air-conditioning apparatus is modified, it is possible to enhance the disinfection/inactivation effect by attaching assist louvers to the existing air-conditioning apparatus to increase the directivity and straightness of the air flow.

Furthermore, in Embodiment 3, the existing air-conditioning apparatus 60 originally provided in the air-conditioning target space, such as an office, may be replaced with an air-conditioning apparatus 60 provided with the disinfecting and virus inactivating device 1. Also, in this case, it is possible to efficiently perform disinfection or virus inactivation in the target space S without changing the appearance of the target space S in the same manner as in the case in which the existing air-conditioning apparatus 60 is modified.

The configuration of each of the air outlets 65 and the arrangement of the air direction plates 66 are not limited to such a configuration and arrangement as described above, and the following configurations as illustrated in FIGS. 16 to 20 may be adopted.

Figure 16:
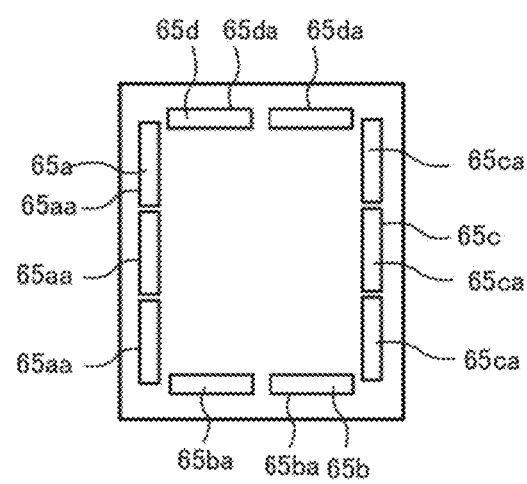
FIG. 16 is a schematic view illustrating of a modification of the air-conditioning apparatus 60 according to Embodiment 3 as viewed from below.
Figure 17:
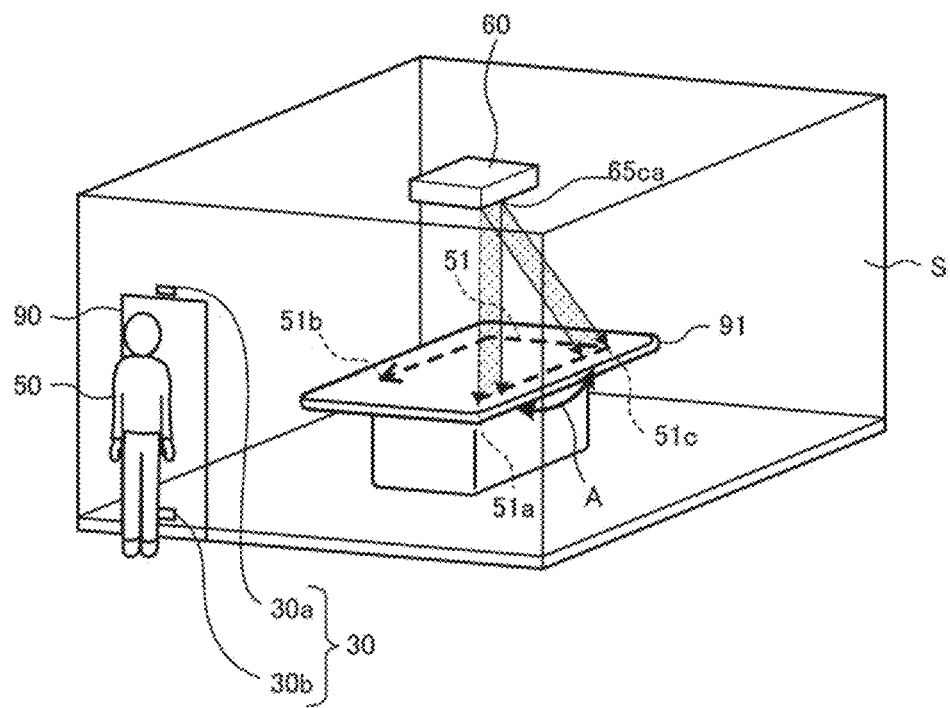
FIG. 17 is a (first) explanatory view for the disinfection/inactivation operation by the air-conditioning apparatus 60 as illustrated in FIG. 16.
Figure 18:
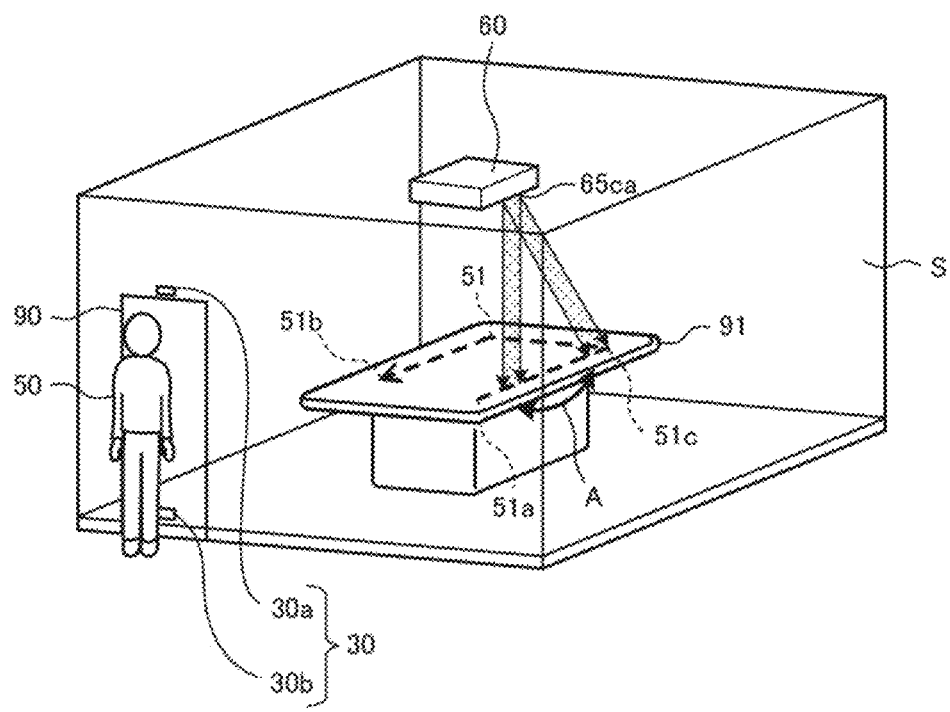
FIG. 18 is a (second) explanatory view for the disinfection/inactivation operation by the air-conditioning apparatus 60 as illustrated in FIG. 16.

FIG. 16 is a schematic view illustrating a modification of the air-conditioning apparatus 60 according to Embodiment 3 as viewed from below. FIG. 17 is a (first) explanatory view for the disinfection/inactivation operation by the air-conditioning apparatus 60 as illustrated in FIG. 16. FIG. 18 is a (second) explanatory view for the disinfection/inactivation operation by the air-conditioning apparatus 60 as illustrated in FIG. 16.

In the modification, as illustrated in FIG. 16, each of the air outlets 65a to 65d located on respective sides is divided into a plurality of outlets. Although not illustrated in FIG. 17 in detail, for divided air outlets 65aa to 65da, respective air direction plates 66 are provided, and each of the air direction plates 66 can independently control the flow direction of air from an associated one of the divided air outlets 65aa to 65da in the vertical direction and the lateral direction. The substance generating modules 32 may be installed in the respective divided air outlets 65aa to 65da, or only one substance generating module 32 may be installed in the air-conditioning apparatus 60 and supply the particular substance to air flows into which the air low is divided by the divided air outlets 65aa to 65da.

FIG. 17 illustrates a state in which an air flow is transmitted from one of the divided air outlets 65ca that is the closest to a front side. FIG. 18 illustrates a state in which an air flow is transmitted from one of the divided air outlets 65ca that is located in the middle thereof. To be more specific, FIGS. 17 and 18 illustrates a state in which an air flow is transmitted in such a manner as to trace an area between the start point 51a and the pass point 51c of the movement locus 51 in the directions indicated by the arrows A. FIGS. 17 and 18 illustrate the state in which an air flow is transmitted only from the divided air outlet 65ca. However, the air flow is transmitted toward the movement locus 51 from one of the divided air outlets 65ba and one of the divided air outlets 65aa in the same manner as described above.

Figure 19:
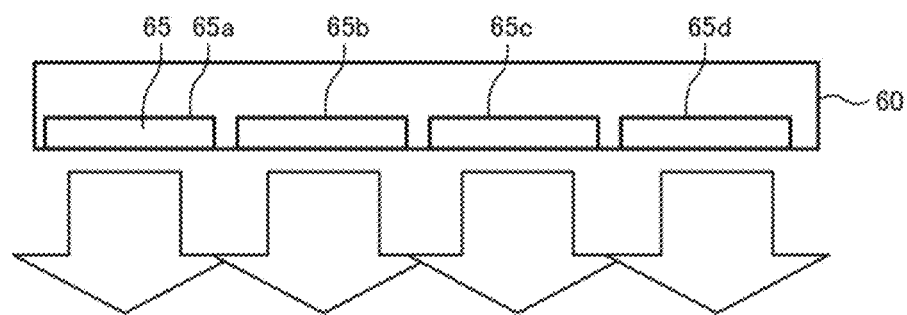
Figure 20:
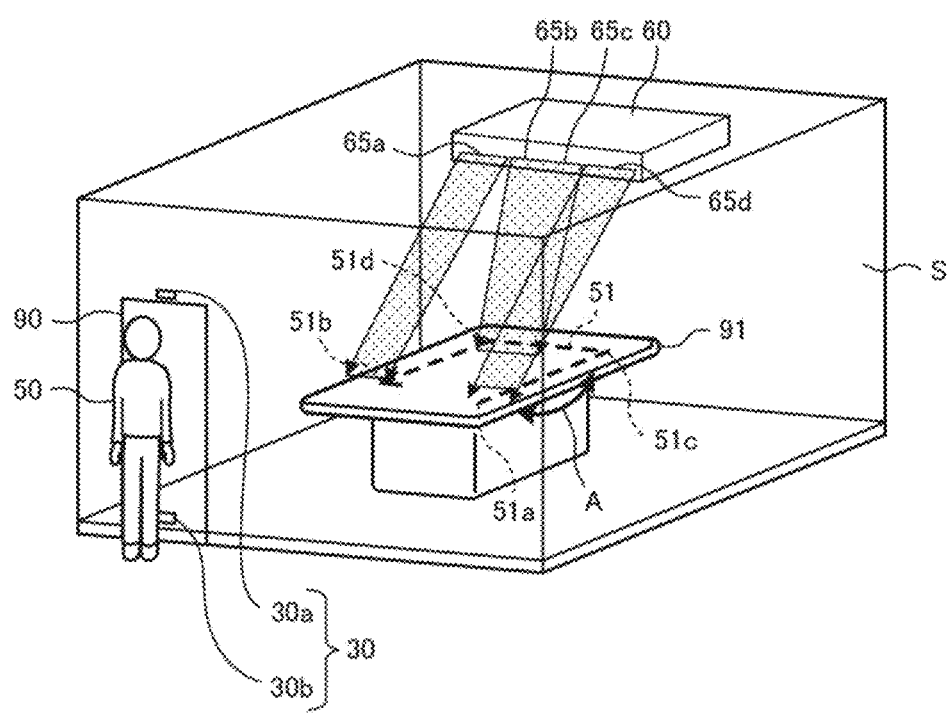
FIG. 20 is an explanatory view for the disinfection/inactivation operation by the air-conditioning apparatus 60 as illustrated in FIG. 19.

FIG. 19 is a schematic view of a modification of the air-conditioning apparatus 60 according to Embodiment 3 as viewed side-on. FIG. 20 is an explanatory view for the disinfection/inactivation operation by the air-conditioning apparatus 60 as illustrated in FIG. 19.

In the modification, as illustrated in FIG. 19, air outlets 65 (65a to 65d) are provided in the side surface of the housing 61. Although not illustrated in FIG. 20 in detail, the air direction plates 66 are individually provided for the respective air outlets 65, and the flow direction of air from each of the air outlets 65 can be independently controlled in the vertical direction and the lateral direction. For the air outlets 65, respective substance generating modules 32 may be provided. Alternatively, only one substance generating module 32 may be provided in the air-conditioning apparatus 60, and may supply the particular substance to air flows into which an air flow is divided by the respective air outlets 65.

FIG. 20 illustrates a state in which an air flow is transmitted from the air outlet 65a to an area between a pass point 51d and the end point 51b of the movement locus 51. FIG. 20 also illustrates a state in which an air flow is transmitted from the air outlets 65b and 65c to an area between the pass point 51c and the pass point 51d of the movement locus 51. FIG. 20 further illustrates a state in which an air flow is transmitted from the air outlet 65d to an area between the start point 51a and the pass point 51c. In such a manner, the disinfecting and virus inactivating device 1 is also applicable to a given type of air-conditioning apparatus 60 in which the air outlets 65 are provided in the side surface of the housing 61.

The modifications of Embodiments 1 and 2 are applicable to the air-conditioning apparatus 60 of Embodiment 3 as appropriate. To be more specific, for example, the operation of enhancing the disinfection/inactivation effect that is performed on the locus overlapping region 52 and that is described above as the modification of Embodiment 1 is applicable to the disinfecting and virus inactivating device 1 of Embodiment 3. Furthermore, the operation of enhancing the disinfection/inactivation effect that is performed on the movement loci 51 of moving bodies in turn from the movement locus 51 of a moving body whose temperature falls within the low temperature zone to the movement locus 51 of a moving body whose temperature falls within the high temperature zone and that is described above as the modification of Embodiment 2 is applicable to the air-conditioning apparatus 60 of Embodiment 3.

Needless to say, in the present disclosure, the above descriptions concerning the embodiments are not limiting, and the embodiments can be various modified and changed within the scope of the present disclosure. It is described above that an office is an example of the target space S in which the disinfecting and virus inactivating device 1 is installed. However, the target space S is not limited to the office, and may be an ordinary house, a storage chamber, or a bathroom, for example. The target space S may also be a space in a refrigerator or a freezer.

REFERENCE SIGNS LIST

1: disinfecting and virus inactivating device, 1a: housing, 2: first casing, 3: second casing, 4: grille body, 4a: grille, 5: blowing port, 6: fin, 6a: inner end portion, 6b: outer end portion, 7: base, 21: cylindrical portion, 23: upper surface portion, 23a: air inlet, 24: ventilation passage, 25: connector, 25a: hook portion, 26: engagement portion, 27: air-passage forming portion, 30: sensing module, 30a: transmission module, 30b: reception module, 31: locus detection module, 31a: photographing module, 31b: image processing module, 31c: infrared-ray detection module, 31d: storage module, 32: substance generating module, 33: transmission module, 34: substance measuring module, 35: main board, 36: display module, 37: blower, 39: driving device, 40: controller, 41: mode changing switch, 42: communication module, 50: person, 51: movement locus, 51a: start point, 51b: end point, 51c: pass point, 52: locus overlapping region, 60: air-conditioning apparatus, 61: housing, 62: main body, 63: decorated panel, 64: suction grille, 65: air outlet, 65a to 65d: air outlet, 65aa to 65da: divided air outlet, 66: air direction plate, 66a: vertical air direction plate, 66b: lateral air direction plate, 67: centrifugal blower, 68: motor, 69: heat exchanger, 70: drain pan, 71: electric component box, 71a: control board, 90: door, 91: furniture, O: central portion, S: target space

The invention claimed is:

1. A disinfecting and virus inactivating device that performs disinfection treatment or inactivation treatment in a target space that a moving body enters and exits, the disinfecting and virus inactivating device comprising:
a locus detection module configured to detect a movement locus of locations on portions of furniture provided in the target space where the moving body comes into contact with the portions of the furniture;
a substance generating module configured to generate a particular substance for use in the disinfection treatment or the inactivation treatment; and
a transmission module configured to generate an air flow and transmit the particular substance generated by the substance generating module to the movement locus,
wherein the locus detection module includes an infrared-ray detection module configured to detect infrared rays emitted from a heat source, and is configured to detect the movement locus of the moving body in the target space based on a result of detection by the infrared-ray detection module,
temperatures of moving bodies are classified into a plurality of temperature zones based on the result of detection by the infrared-ray detection module, including a high temperature zone and a low temperature zone, and either one or both of the substance generating module and the transmission module are operated such that disinfection/virus-inactivation has a greater disinfection/inactivation effect on a movement locus of one moving body whose temperature falls within the high temperature zone, than on a movement locus of another moving body whose temperature falls within the low temperature zone, and
the transmission module is configured to direct the air flow containing the particular substance from the movement locus of a moving body whose temperature falls within the high temperature zone to the movement locus of a moving body whose temperature falls within the low temperature zone.

2. The disinfecting and virus inactivating device of claim 1, wherein the transmission module includes a blower, a grille, and a driving device, the blower being configured to generate the air flow, the grille being provided downstream of the blower and being configured to give straightness and directivity to the air flow from the blower, the driving device being configured to control a blowing direction of the air flow by changing an orientation of the grille, and
the transmission module is configured to transmit the air flow in such a manner as to cause the air flow to trace the movement locus, by changing the orientation of the grille by the driving device.

3. The disinfecting and virus inactivating device of claim 1, further comprising a sensing module configured to detect that the moving body exits the target space,
wherein the transmission module is configured to transmit the particular substance generated by the substance generating module to the movement locus, when the sensing module detects that the moving body exits the target space.

4. The disinfecting and virus inactivating device of claim 3, wherein the transmission module is configured to transmit the particular substance generated by the substance generating module to the movement locus after a given time period set in advance elapses, when the sensing module detects that the moving body exits the target space.

5. The disinfecting and virus inactivating device of claim 1, wherein either one or both of the substance generating module and the transmission module are operated such that disinfection/virus-inactivation has a greater disinfection/inactivation effect on a locus overlapping region where a plurality of movement loci overlap with each other, than on a region other than the locus overlapping region.

6. The disinfecting and virus inactivating device of claim 5, wherein either one or both of the substance generating module and the transmission module perform, as an operation of enhancing the disinfection/inactivation effect, one or more or all of an operation of increasing a blowing amount of air from the transmission module, an operation of increasing an amount of generation of the particular substance, and an operation of increasing time for which the particular substance is transmitted.

7. The disinfecting and virus inactivating device of claim 1, wherein the transmission module is configured to operate in such a manner as to obtain an amount of the air flow that is larger than or equal to a set amount of air necessary for ensuring comfort.

8. The disinfecting and virus inactivating device of claim 1, wherein the substance generating module is configured to generate the particular substance such that a concentration of the particular substance in the target space reaches a concentration of the particular substance that is effective for efficient disinfection or virus inactivation, when the particular substance has a relatively low persistence.

9. The disinfecting and virus inactivating device of claim 1, wherein the substance generating module is configured to generate the particular substance such that a concentration of the particular substance in the target space does not exceed a set concentration set in advance, when the particular substance has a relatively high persistence.

10. An air-conditioning apparatus comprising:
the disinfecting and virus inactivating device of claim 1; and
a heat exchanger configured to cause heat exchange to be performed between air and refrigerant that flows in the heat exchanger,
the air-conditioning apparatus transmitting to the movement locus, an air flow that passes through the heat exchanger and is thus conditioned in temperature and that contains the particular substance.

11. A method of performing disinfection or virus inactivation in which disinfection treatment or inactivation treatment is performed in a target space that a moving body enters and exits, the method comprising:

detecting a movement locus of locations on portions of furniture provided in the target space where the moving body comes into contact with the portions of the furniture; and causing a transmission module to generate an air flow and transmit a particular substance generated by a substance generating module to the movement locus, as disinfection or virus inactivation, detecting infrared rays emitted from a heat source;

detecting the movement locus of the moving body in the target space based on the detecting infrared rays;

classifying temperatures of moving bodies into a plurality of temperature zones based on the detecting infrared rays, including a high temperature zone and a low temperature zone;

causing the transmission module to generate and transmit the particular substance such that disinfection/virus-inactivation has a greater disinfection/inactivation effect on a movement locus of one moving body whose temperature falls within the high temperature zone, than on a movement locus of another moving body whose temperature falls within the low temperature zone; and directing the air flow containing the particular substance from the movement locus of a moving body whose temperature falls within the high temperature zone to the movement locus of a moving body whose temperature falls within the low temperature zone.

12. The method of performing disinfection or virus inactivation of claim 11, wherein the locus detection is started when it is detected that the moving body enters the target space, and the locus detection is ended when it is detected that the moving body exits the target space, and the disinfection or virus inactivation is started when it is detected that the moving body exists the target space.

13. The disinfecting and virus inactivating device of claim 1, wherein the locus detection module is configured to detect the movement locus by performing difference processing based on background data.

* * * * *